United States Patent
Nitta et al.

(10) Patent No.: US 10,459,057 B2
(45) Date of Patent: Oct. 29, 2019

(54) IMAGE PROCESSING APPARATUS, MAGNETIC RESONANCE IMAGING APPARATUS AND IMAGE PROCESSING METHOD

(71) Applicant: TOSHIBA MEDICAL SYSTEMS CORPORATION, Otawara-shi, Tochigi (JP)

(72) Inventors: Shuhei Nitta, Tokyo (JP); Taichiro Shiodera, Tokyo (JP); Tomoyuki Takeguchi, Kanagawa (JP); Masao Yui, Tochigi (JP); Satoshi Sugiura, Tochigi (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1090 days.

(21) Appl. No.: 14/820,933

(22) Filed: Aug. 7, 2015

(65) Prior Publication Data

US 2015/0338489 A1   Nov. 26, 2015

Related U.S. Application Data

(63) Continuation of application No. PCT/JP2014/052450, filed on Feb. 3, 2014.

(30) Foreign Application Priority Data

Feb. 8, 2013  (JP) .................................. 2013-023037

(51) Int. Cl.
*G01R 33/563* (2006.01)
*G01R 33/54* (2006.01)
(Continued)

(52) U.S. Cl.
CPC .......... *G01R 33/5635* (2013.01); *A61B 5/055* (2013.01); *A61B 5/14507* (2013.01);
(Continued)

(58) Field of Classification Search
USPC ......................... 324/300–322; 600/407–435; 382/128–131
See application file for complete search history.

(56) References Cited

U.S. PATENT DOCUMENTS 7,684,604 B2    3/2010   Bystrov et al. ............... 128/131
8,380,281 B2 *  2/2013   Osman ................... A61B 5/702
                                                                600/407
(Continued)

FOREIGN PATENT DOCUMENTS

CN       102028465 A      4/2011
JP       2003-144416 A    5/2003
(Continued)

OTHER PUBLICATIONS

Office Action dated Mar. 7, 2017 in JP 2013-023037.
(Continued)

*Primary Examiner* — Melissa J Koval
*Assistant Examiner* — Tiffany A Fetzner
(74) *Attorney, Agent, or Firm* — Nixon & Vanderhye P.C.

(57) ABSTRACT

An image processing apparatus according to an embodiment includes processing circuitry. The processing circuitry is configured to detect a region of body fluid flowing in a subject from time-series images acquired by scanning an imaging area including a tagged region to which a tagging pulse is applied and imaging the imaging area; generate a plurality of display images in which the detected body fluid region is displayed in a display mode determined based on a positional relation between the body fluid region and a boundary line, the boundary line determined based on the
(Continued)

tagged region; and output time-series display images including the plurality of display images to be displayed on a display.

14 Claims, 16 Drawing Sheets

(51) Int. Cl.
| | | |
|---|---|---|
| G01R 33/56 | (2006.01) | |
| A61B 5/145 | (2006.01) | |
| A61B 5/055 | (2006.01) | |
| A61B 5/00 | (2006.01) | |

(52) U.S. Cl.
CPC ....... *G01R 33/543* (2013.01); *G01R 33/5608* (2013.01); *G01R 33/56333* (2013.01); *A61B 5/0042* (2013.01); *A61B 5/7292* (2013.01)

(56) References Cited

U.S. PATENT DOCUMENTS

| | | | | |
|---|---|---|---|---|
| 8,441,257 B2* | 5/2013 | Mordini | ........... | G01R 33/56366 324/309 |
| 8,515,526 B2* | 8/2013 | Miyazaki | ............... | A61B 5/055 600/410 |
| 8,624,591 B2 | 1/2014 | Kimura | ........................ | 324/306 |
| 8,890,521 B2 | 11/2014 | Shinoda et al. | ............. | 324/307 |
| 9,474,455 B2* | 10/2016 | Miyazaki | ........... | G01R 33/5635 |
| 9,585,576 B2* | 3/2017 | Miyazaki | ........... | G01R 33/5635 |
| 9,839,366 B2* | 12/2017 | Miyazaki | ........... | G01R 33/5635 |
| 10,058,257 B2* | 8/2018 | Miyazaki | ........... | G01R 33/5635 |
| 2008/0061780 A1 | 3/2008 | Yamada et al. | ................ | 324/309 |
| 2009/0005670 A1 | 1/2009 | Ichinose et al. | ............. | 600/410 |
| 2010/0087730 A1 | 4/2010 | Yamada et al. | ................ | 600/419 |
| 2010/0198053 A1* | 8/2010 | Miyazaki | ................ | A61B 5/055 600/419 |
| 2011/0071382 A1* | 3/2011 | Miyazaki | ........... | G01R 33/5635 600/413 |
| 2011/0074416 A1 | 3/2011 | Yamashita et al. | ........... | 324/309 |
| 2011/0260725 A1* | 10/2011 | Mordini | ........... | G01R 33/56325 324/309 |
| 2011/0270079 A1* | 11/2011 | Osman | .................... | A61B 5/702 600/421 |
| 2012/0256627 A1 | 10/2012 | Furudate | ....................... | 324/309 |
| 2013/0253307 A1* | 9/2013 | Miyazaki | ........... | G01R 33/5635 600/419 |
| 2015/0338489 A1* | 11/2015 | Nitta | .................. | A61B 5/14507 324/309 |

FOREIGN PATENT DOCUMENTS

| | | |
|---|---|---|
| JP | 3895972 | 3/2007 |
| JP | 2009-28525 A | 2/2009 |
| JP | 2009-247773 A | 10/2009 |
| JP | 4368988 | 11/2009 |
| JP | 2010-88515 A | 4/2010 |
| JP | 4594482 | 12/2010 |
| JP | 2011-92670 | 5/2011 |
| JP | 2011-183152 | 9/2011 |
| JP | 4771490 | 9/2011 |
| JP | 2012-125554 A | 7/2012 |
| JP | 2012-223557 A | 11/2012 |

OTHER PUBLICATIONS

International Search Report dated Apr. 28, 2014 in PCT/JP2014/052450.
Chinese office action dated Apr. 26, 2017, in Patent Application No. CN 201480007534.5.

* cited by examiner

IMAGE PROCESSING APPARATUS, MAGNETIC RESONANCE IMAGING APPARATUS AND IMAGE PROCESSING METHOD

CROSS-REFERENCE TO RELATED APPLICATIONS

This application is a continuation of PCT international application Ser. No. PCT/JP2014/052450 filed on Feb. 3, 2014 which designates the United States, incorporated herein by reference, and which claims the benefit of priority from Japanese Patent Application No. 2013-023037, filed on Feb. 8, 2013, the entire contents of which are incorporated herein by reference.

FIELD

Embodiments described herein relate generally to an image processing apparatus and a magnetic resonance imaging apparatus.

BACKGROUND

The magnetic resonance imaging is an imaging method of generating an image from data including a magnetic resonance signal generated associated with magnetic excitation by a radio frequency (RF) pulse having the Larmor frequency for nuclear spins of a subject placed in a static magnetic field. In the field of the magnetic resonance imaging, the magnetic resonance angiography (MRA) has been known as a method of generating an image of body fluid flowing in a subject, without using a contrast agent, for example.

In arterial spin labeling (ASL) or a time-spatial labeling inversion pulse (Time-SLIP) method, for example, the body fluid such as blood or cerebrospinal fluid (hereinafter referred to as "CSF" as appropriate) are magnetically tagged by applying a tagging pulse, thereby being visualized without using a contrast agent.

DETAILED DESCRIPTION

An image processing apparatus according to an embodiment includes processing circuitry. The processing circuitry is configured to detect a region of body fluid flowing in a subject from time-series images acquired by scanning an imaging area including a tagged region to which a tagging pulse is applied and imaging the imaging area; generate a plurality of display images in which the detected body fluid region is displayed in a display mode determined based on a positional relation between the body fluid region and a boundary line, the boundary line determined based on the tagged region; and output time-series display images including the plurality of display images to be displayed on a display.

Hereinafter, an image processing apparatus and a magnetic resonance imaging (MRI) apparatus according to an embodiment will be described with reference to accompanying drawings. Embodiments are not limited to the embodiments described below. The details described in each of the following embodiments can, in principle, be applied to other embodiments in the same manner. It is noted that "tagging" may also be called "labeling" and the "tagging pulse" may also be called a "tag pulse" and "labeling pulse".

First Embodiment

Figure 1:
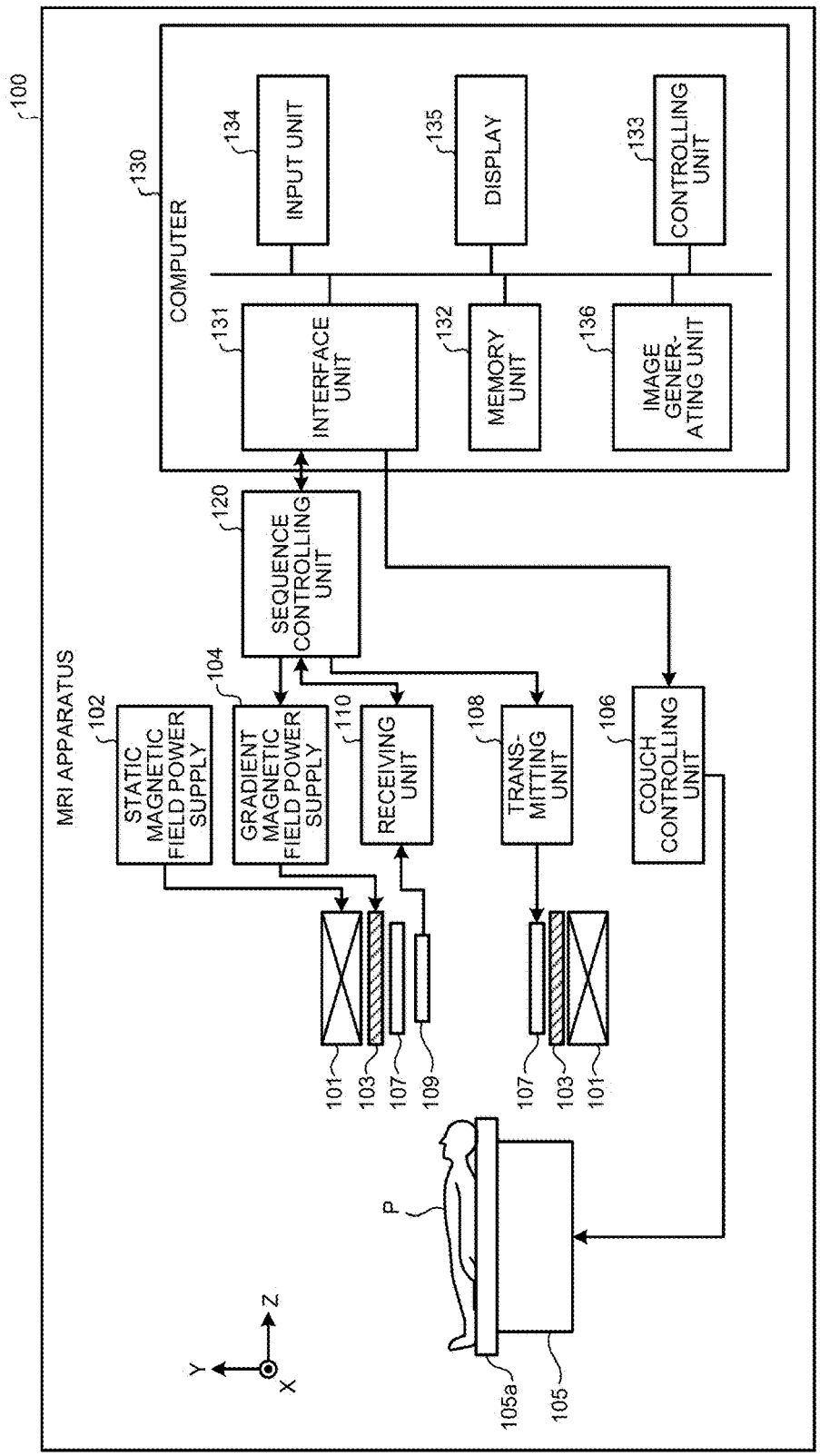
FIG. 1 is a block diagram illustrating the configuration of a magnetic resonance angiography (MRA) apparatus related to some embodiment.

FIG. 1 is a block diagram illustrating the configuration of an MRI apparatus 100 related to some embodiment. As illustrated in FIG. 1, the MRI apparatus 100 includes a static magnetic field magnet 101, a static magnetic field power supply 102, a gradient coil 103, a gradient magnetic field power supply 104, a couch 105, a couch controlling unit 106, a transmitting coil 107, a transmitting unit 108, a receiving coil 109, a receiving unit 110, a sequence controlling unit 120, and a computer 130. The MRI apparatus 100 does not include a subject P (e.g., a human body). The configuration illustrated in FIG. 1 is merely an example. The sequence controlling unit 120 and the computer 130 may be configured integrally or separately as appropriate, for example.

The static magnetic field magnet 101 is a magnet in a hollowed cylindrical shape that generates a static magnetic field in its inside space. The static magnetic field magnet 101 is a superconducting magnet, for example, that receives a power supply from the static magnetic field power supply 102 to excite the magnetic field. The static magnetic field power supply 102 supplies the static magnetic field magnet 101 with an electric current. The static magnetic field magnet 101 may be a permanent magnet, which allows the MRI apparatus 100 to include no static magnetic field power supply 102. Alternatively, the static magnetic field power supply 102 may be provided separately from the MRI apparatus 100.

The gradient coil 103 is a coil in a hollowed cylindrical shape and disposed inside of the static magnetic field magnet 101. The gradient coil 103 includes three coils each corresponding to axes X, Y, and Z orthogonal to each other. The three coils each receive a power supply from the gradient magnetic field power supply 104 and generate gradient magnetic fields having different magnetic field strengths in the respective fields along the axes X, Y, and Z. The gradient magnetic fields along the axes X, Y, and Z generated by the gradient coil 103 are, for example, a gradient magnetic field for slicing Gs, a gradient magnetic field for phase encoding Ge, and a gradient magnetic field for reading Gr. The gradient magnetic field power supply 104 supplies the gradient coil 103 with an electric current.

The couch 105 includes a couchtop 105a on which a subject P is placed. The couch 105 inserts the couchtop 105a with the subject P placed thereon into a hollow (an opening for imaging) of the gradient coil 103 under the control of the couch controlling unit 106. The couch 105 is usually provided so as to have its longitudinal direction parallel to the central axis of the static magnetic field magnet 101. The couch controlling unit 106 drives the couch 105 to move the couchtop 105a in its longitudinal direction and its vertical direction under the control of the computer 130.

The transmitting coil 107 disposed inside of the gradient coil 103 receives RF pulses supplied from the transmitting unit 108 and generates a high-frequency magnetic field. The transmitting unit 108 supplies the transmitting coil 107 with the RF pulses corresponding to the Larmor frequency determined by the type of the target atom and the magnetic field strength.

The receiving coil 109 disposed inside of the gradient coil 103 receives a magnetic resonance signal (hereinafter referred to as an "MR signal" as appropriate) emitted from the subject P under the influence of the high-frequency magnetic field. Upon receiving the MR signal, the receiving coil 109 outputs the received MR signal to the receiving unit 110.

The transmitting coil 107 and the receiving coil 109 are described above merely for exemplary purpose and are not limiting. One or more coils may be used out of the coils such as a coil including a transmitting function only and a coil including a receiving function only.

The receiving unit 110 detects the MR signal output from the receiving coil 109 and generates a piece of MR data based on the detected MR signal. Specifically, the receiving unit 110 converts the MR signal output from the receiving coil 109 into a digital signal to generate the MR data. The receiving unit 110 transmits the generated MR data to the sequence controlling unit 120. It is noted that the receiving unit 110 may be provided on the side of a gantry device including the static magnetic field magnet 101 and the gradient coil 103.

The sequence controlling unit 120 drives the gradient magnetic field power supply 104, the transmitting unit 108, and the receiving unit 110 to capture an image of the subject P based on sequence information transmitted from the computer 130. The sequence information defines the procedure for capturing images, that is, imaging. The sequence information defines the following, for example: the strength and the timing of the current supplied by the gradient magnetic field power supply 104 to the gradient coil 103; the strength of the RF pulse supplied by the transmitting unit 108 to the transmitting coil 107 or the application timing of the RF pulse; and the timing of detecting the MR signal by the receiving unit 110. For example, the sequence controlling unit 120 is an integrated circuit such as an application specific integrated circuit (ASIC) and a field programmable gate array (FPGA). For another example, the sequence controlling unit 120 is an electronic circuit such as a central processing unit (CPU) and a micro processing unit (MPU).

After the sequence controlling unit 120 drives the gradient magnetic field power supply 104, the transmitting unit 108, and the receiving unit 110 to capture an image of the subject P and receives the MR data from the receiving unit 110, the sequence controlling unit 120 transfers the received MR data to the computer 130.

The computer 130 controls the MRI apparatus 100 totally and generates an image. The computer 130 includes an interface unit 131, a memory unit 132, a controlling unit 133, an input unit 134, a display 135, and an image generating unit 136.

The interface unit 131 transmits the sequence information to the sequence controlling unit 120 and receives the MR data from the sequence controlling unit 120. After receiving the MR data, the interface unit 131 stores the received MR data in the memory unit 132. The MR data stored in the memory unit 132 is disposed in the k-space by the controlling unit 133. This operation allows the memory unit 132 to store k-space data therein.

The memory unit 132 stores therein the MR data received by the interface unit 131, the k-space data disposed in the k-space by the controlling unit 133, and the image data generated by the image generating unit 136. For example, the memory unit 132 is a semiconductor memory device such as a random access memory (RAM) and a flash memory, or alternatively a hard disk, or an optical disc, and the like.

The input unit 134 receives various types of instructions and information input from an operator. For example, the input unit 134 is a pointing device such as a mouse and a trackball. For another example, the input unit 134 is a selection device such as a mode switch, or an input device such as a keyboard. The display 135 displays a graphical user interface (GUI) for receiving an input of imaging conditions and an image generated by the image generating unit 136 under the control of the controlling unit 133. The display 135 is a display device such as a liquid crystal display device.

The controlling unit 133 controls the MRI apparatus 100 totally and controls imaging, generation of images, and display of images. The processes executed by the controlling unit 133 will be described in detail later.

The image generating unit 136 reads the k-space data from the memory unit 132 and executes reconstruction processing on the k-space data such as the Fourier transform, thereby generating an image.

In the first embodiment, the MRI apparatus 100 collects, on a time-series basis, images in which the CSF existing in the brain of the subject is visualized and generates an image to be displayed (a display image) for each of the collected images, and then displays the display image on the display 135. The MRI apparatus 100 collects the images using the Time-SLIP method. In the first embodiment, the images are collected using the Time-SLIP method. This method is provided merely for exemplary purpose and not limiting. Any other method may be used for collecting images of body fluid flowing in the subject depending on the purpose of the imaging and the form of the operation of images.

Figure 2:
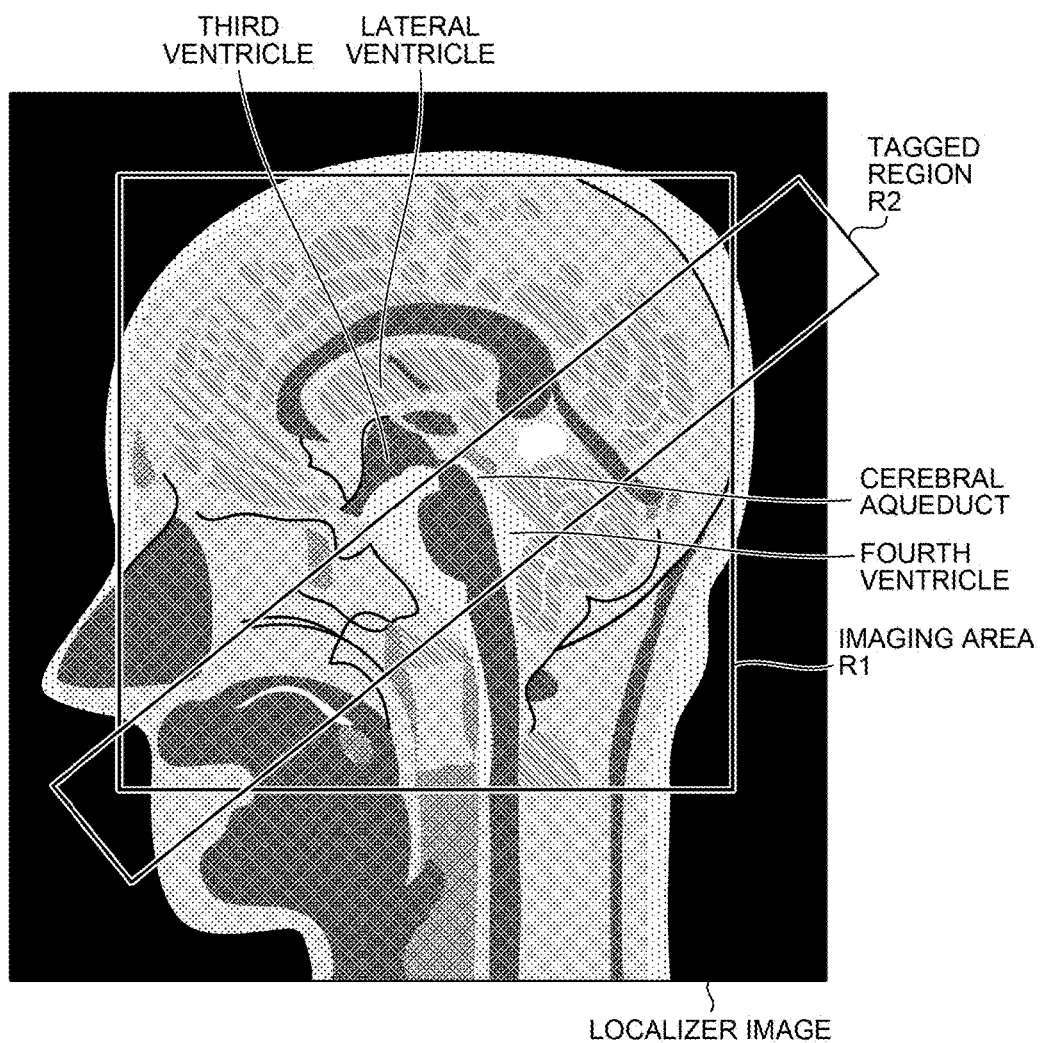
FIG. 2 is a diagram for explaining a time-spatial labeling inversion pulse (Time-SLIP) method applied to some embodiments.
Figure 3A:
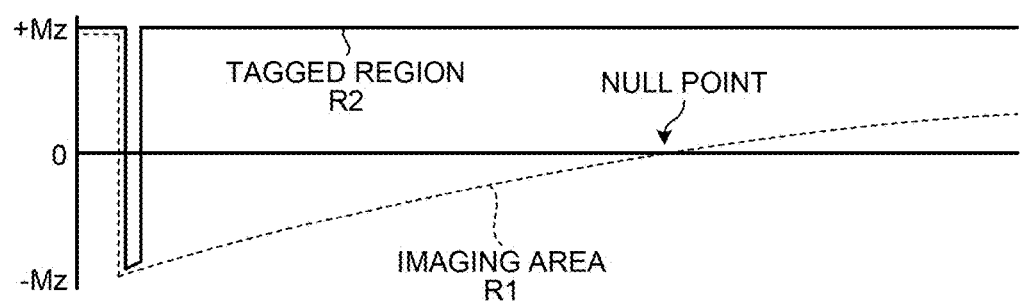
FIGS. 3A and 3B are diagrams for explaining the Time-SLIP method applied to some embodiments.
Figure 3B:
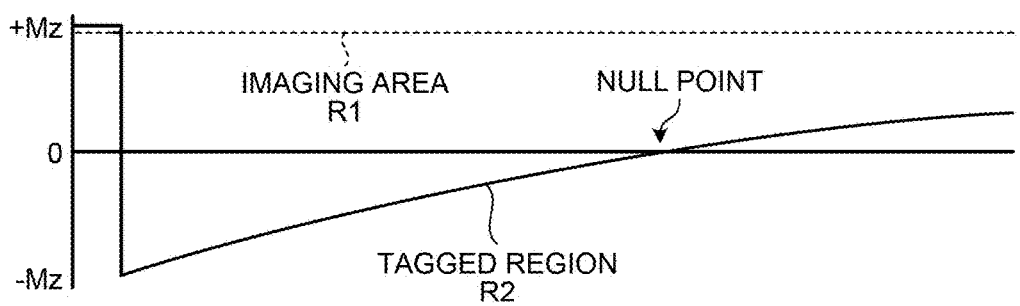

FIGS. 2 to 3B are diagrams for explaining the Time-SLIP method applied to the first embodiment. In the Time-SLIP method, a tagging pulse is applied to a tagged region defined independently from an imaging area, thereby tagging body fluid within the tagged region. After a given time elapses, the signal value of the body fluid flows into or flows out of the imaging area is relatively increased or decreased, thereby selectively drawing the body fluid. For example, FIG. 2 illustrates that an imaging area R1 and a tagged region R2 are defined on a localizer image that is a sagittal image of the brain. The imaging area R1 is defined, for example, so as to include the lateral ventricles, the third ventricle, the cerebral aqueduct, and the fourth ventricle. The tagged region R2 is defined in a range, for example, from the top end of the cerebral aqueduct to the bottom end of the fourth ventricle. The above-described definitions of the imaging area and the tagged region are provided merely for exemplary purpose and not limiting. The imaging area and the tagged region may be selectively defined so that the dynamic state of body fluid may be visualized depending on the purpose of the imaging.

In the Time-SLIP method, the tagging pulse has two types: a spatial non-selective pulse and a spatial-selective pulse. At some times, the spatial non-selective pulse may not be applied. FIGS. 3A and 3B illustrate that if an inversion recovery (IR) pulse is applied as a tagging pulse, the longitudinal magnetization (represented with a unit of Mz) on tissues relaxes.

FIG. 3A illustrates an example, where a spatial non-selective IR pulse is firstly applied to the imaging area R1 and at or nearly at the same time, a spatial-selective IR pulse is applied to the tagged region R2 in the imaging area R1. On this occasion, the application of the spatial non-selective IR pulse inverts the longitudinal magnetization of the tissues within the imaging area R1, as illustrated in FIG. 3A, from a positive value to a negative value. The application of the spatial selective IR pulse inverts again the longitudinal magnetization of the tissues within the tagged region R2, as illustrated in FIG. 3A, from a negative value to a positive value. The longitudinal magnetization of the tissues within the imaging area R1 excluding the tagged region R2 gradually relaxes (restores to its original state) and reaches the null point at which the background tissue has a signal value of zero. For example, body fluid each having a positive signal value in response to the inverted longitudinal magnetization within the tagged region R2 flows out to the imaging area R1. In this state, if pieces of image data are collected for a period including the null point, or at a timing of or after the null point, the signal value of the body fluid tagged within the tagged region R2 relatively increases in the imaging area R1, thereby selectively drawing body fluid. This operation may be called a flow-out method.

FIG. 3B illustrates an example, where only the spatial-selective IR pulse is applied to the tagged region R2 without application of the spatial non-selective IR pulse. The tagged region R2 here is defined outside of the imaging area R1. On this occasion, as illustrated in FIG. 3B, the longitudinal magnetization of the tissues within the imaging area R1 maintains its state, and the longitudinal magnetization of the tissues within the tagged region R2 inverts from a positive value to a negative value. The longitudinal magnetization of the tissues that receives the spatial-selective IR pulse within the tagged region R2 gradually relaxes (restores to its original state) and reaches the null point at which the tissue has a signal value of zero. For example, body fluid each having a negative signal value in response to the inverted longitudinal magnetization within the tagged region R2 flows into the imaging area R1. In this state, if pieces of image data are collected for a period including the null point, for example, or at a timing of or after the null point, the signal value of the body fluid tagged within the tagged region R2 relatively decreases in the imaging area R1, thereby selectively drawing body fluid. This operation may be called a flow-in method.

The method illustrated in FIGS. 3A and 3B is merely an example. The above-described definitions of the flow-out method and the flow-in method are also provided merely for exemplary purpose and not limiting. The opposite or other names may be used for the methods depending on the way of definition. The following may be arbitrarily selected depending on the purpose of the imaging: whether the tagged region is defined inside or outside of the imaging area; whether one or more of tagged regions are defined; whether the spatial non-selective pulse is applied or not; whether the tagging pulse is applied once or a plurality of times; and at which timing the image data are collected. The period of time from the application of the tagging pulse to the collection of the image data may be called inversion time (TI) or a black blood time to inversion (BBTI). As described later, in the first embodiment, time-series images are collected, for example. For example, the spatial non-selective IR pulse and the spatial-selective IR pulse are applied triggered by the R wave of the electrocardiogram (ECG) signal. After that, the k-space data for a slice encoding are collected for a plurality of time phases within one repetition time (TR). For this reason, the TI and the BBTI are defined a plurality of times, for a period including the null point, for example, or at a timing of after the null point in some embodiments.

In addition, the tagging pulse is not limited to the IR pulse. For another example, the tagging pulse is a saturation (SAT) pulse, a spatial modulation of magnetization (SPAMM) pulse, or a delay alternating with nutation for tailored excitation (DANTE) pulse. The SAT pulse tilts the magnetization vector in the tagged region by 90 degrees to saturate the longitudinal magnetization. For example, in some embodiments, imaging conditions is made so as to apply not only a single SAT pulse but also a plurality of SAT pulses. If a plurality of SAT pulses are applied, for example, a plurality of tagged regions is defined in a radial pattern or a striped pattern in some embodiments. The SPAMM pulse is applied in a spatial-non-selective manner, which is capable of forming a saturated region in a desired pattern such as a striped pattern, a grid pattern, and a radial pattern, by adjusting the gradient magnetic field. The DANTE pulse is also capable of forming a saturated region in a desired pattern such as a striped pattern, a grid pattern, and a radial pattern. The SPAMM pulse and the DANTE pulse are equivalent to a plurality of SAT pulses applied at the same time. In addition, the tagging pulse is adopt some or all of the IR pulse, the SAT pulse, the SPAMM pulse, and the DANTE pulse in a combined manner as appropriate in some embodiments.

Figure 4:
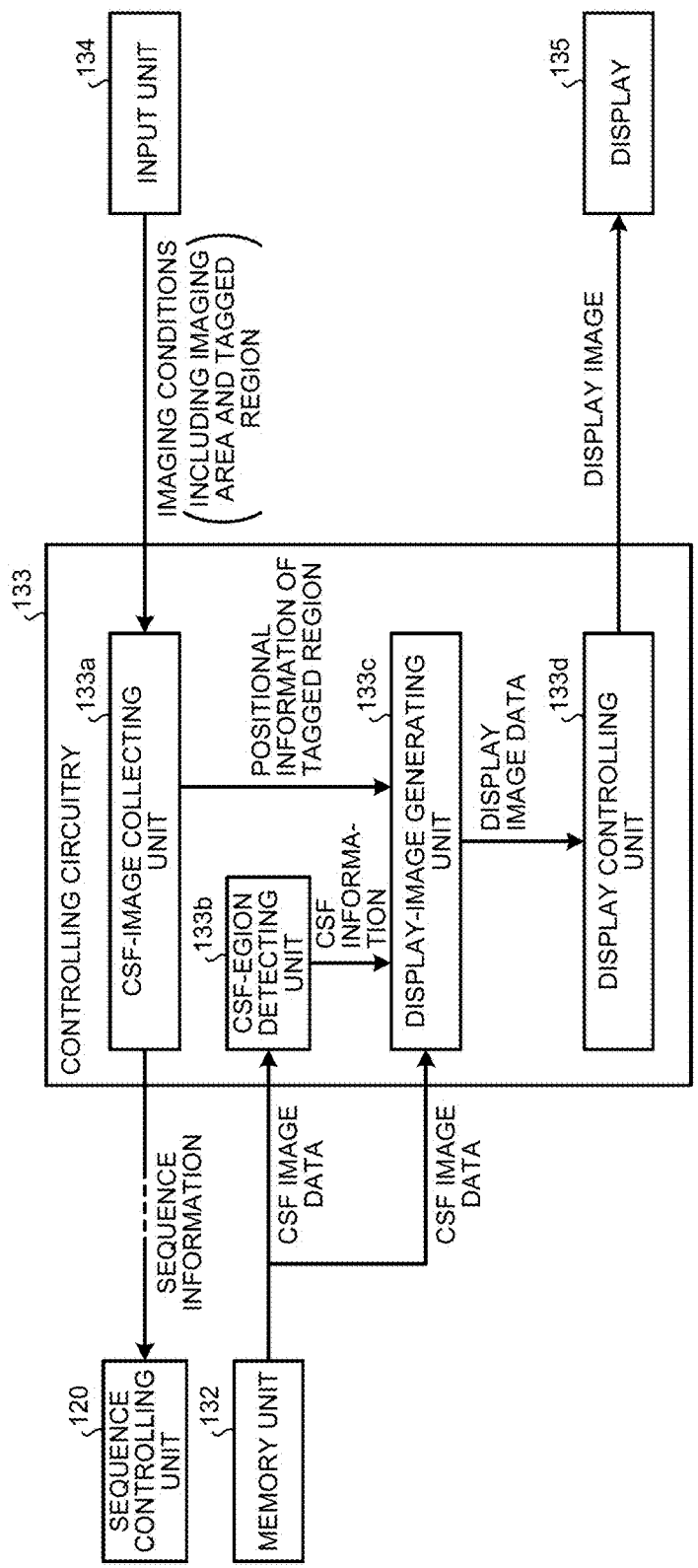
FIG. 4 is a block diagram illustrating the configuration of a controlling unit relating to some embodiments.

FIG. 4 is a block diagram illustrating the configuration of the controlling unit 133 according to the first embodiment. As illustrated in FIG. 4, the controlling unit 133 includes a CSF-image collecting unit 133a, a CSF-region detecting unit 133b, a display-image generating unit 133c, and a display controlling unit 133d.

The CSF-image collecting unit 133a generates sequence information based on the imaging conditions input by an operator through the input unit 134, and transmits the generated sequence information to the sequence controlling unit 120, thereby collecting the k-space data of an image in which the CSF is visualized (hereinafter referred to as a "CSF image" as appropriate). As described later, in the first embodiment, the CSF-image collecting unit 133a collects the k-space data of the time-series CSF images. The image generating unit 136 executes reconstruction processing on the k-space data collected by the CSF-image collecting unit 133a, thereby generating CSF image data, which is then stored in the memory unit 132. For example, in some embodiments, the time-series CSF images are handled as a moving image. Examples of the imaging conditions include positional information of the tagged region defined on the localizer image, which is transmitted by the CSF-image collecting unit 133a to the display-image generating unit 133c.

The CSF-region detecting unit 133b reads from the memory unit 132 the CSF image data collected by the CSF-image collecting unit 133a and subjected to reconstruction processing executed by the image generating unit 136. The CSF-region detecting unit 133b then detects a tagged CSF region (hereinafter referred to as a "CSF region" as appropriate) from the CSF image data. The CSF-region detecting unit 133b transmits to the display-image generating unit 133c the CSF information representing the position and the signal value of the CSF region, for example.

The display-image generating unit 133c receives from the CSF-image collecting unit 133a the positional information of the tagged region defined on the localizer image and receives from the CSF-region detecting unit 133b the CSF information. The display-image generating unit 133c reads from the memory unit 132 the CSF image data collected by the CSF-image collecting unit 133a. Subsequently, the display-image generating unit 133c generates image data in which the CSF region is overlaid on the CSF image in the display mode based on the positional relation between the CSF region and the tagged region (hereinafter referred to as "display image data" as appropriate), and transmits the generated display image data to the display controlling unit 133d. For example, the display-image generating unit 133c classifies the CSF region by using different colors inside of the tagged region and outside of the tagged region, and overlays the color-coded CSF region on the CSF image, thereby generating display image data.

The positional information of the tagged region is not necessarily acquired from imaging conditions. For example, the display-image generating unit 133c executes some image processing such as threshold processing and edge detection processing on the CSF image data having a short elapsed time and a clear contrast between the imaging area and the tagged region out of the time-series CSF images, thereby detecting the tagged region. For another example, the display-image generating unit 133c displays the CSF image on the display 135 to receive a specification of the tagged region by the operator thereon.

The display controlling unit 133d uses the display image data received from the display-image generating unit 133c to display the display images corresponding to the time-series CSF images on the display 135.

The following describes in detail the method for generating the display image data with which the various types of information are overlaid. Examples of the method include: a method for generating the display image data by using a plurality of layers; and a method for generating the display image data by using an overlaid image. With the method for generating the display image data by using a plurality of layers, the display-image generating unit 133c executes image processing such as display contrast setting on the CSF image data read from the memory unit 132, thereby generating the underlying layer of the CSF image. The display-image generating unit 133c also generates a layer of the CSF region and a layer of the tagged region. Subsequently, the display controlling unit 133d overlays the pieces of display image data of the layers generated by the display-image generating unit 133c and displays the overlaid image on the display 135. For example, in some embodiments, the layers described above are defined in another way. For example, one is a layer of the CSF image and the other is a layer of the CSF region and the tagged region. By contrast, with the method for generating the display image data by using an overlaid image, the display-image generating unit 133c overlays the CSF image data, the CSF region and the tagged region with each other, and executes image processing such as display contrast setting on the overlaid image, thereby generating the display image data. Subsequently, the display controlling unit 133d displays the display image data generated by the display-image generating unit 133c as is on the display 135. That is, the difference between the above-described two methods is whether overlaying is executed on the side of display control processing of the display image, or on the side of generation processing of the display image.

The display-image generating unit 133c typically generates the display image data and transmits the generated display image data to the display controlling unit 133d at any appropriate timing for display while the display controlling unit 133d displays the display images. If an operator changes the display contrast setting while the display image is displayed, for example, the display-image generating unit 133c generates the display image data while reflecting the received display contrast setting thereon in real time and transmits the generated data to the display controlling unit 133d. The above-described methods for generating the display image data by the display-image generating unit 133c are provided merely for exemplary purpose and not limiting. The method is modified depending on the form of the operation of images in some embodiments. For another example, the display-image generating unit 133c preliminarily generates a series of the time-series display image data and then transmits the series of the display image data at a time to the display controlling unit 133d.

Figure 5:
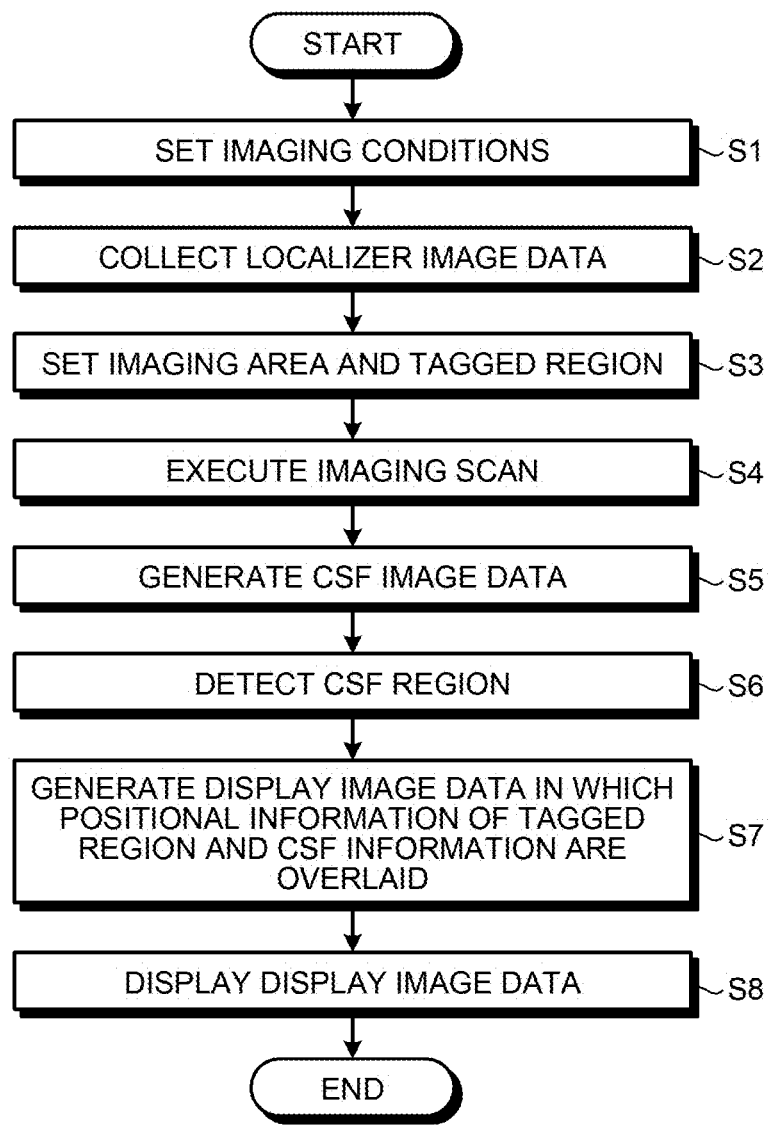
FIG. 5 is a flowchart illustrating processing procedures relating to some embodiments.

FIG. 5 is a flowchart illustrating processing procedure according to the first embodiment. The processing procedure illustrated in FIG. 5 is merely an example and is arbitrarily modified depending on the purpose of the imaging and the form of the operation of images.

Firstly, the CSF-image collecting unit 133a displays a GUI on the display 135 to receive an input of the imaging conditions. The CSF-image collecting unit 133a receives an input of the imaging conditions by the operator and sets the input imaging condition (Step S1). For example, the CSF-image collecting unit 133a sets the imaging condition for acquiring an localizer image and the imaging condition for executing an imaging scan (e.g., a repetition time (TR), an echo time (TE), an imaging area of the localizer image).

Subsequently, the CSF-image collecting unit 133a generates the sequence information according to the imaging condition set at Step S1 and transmits, the generated sequence information to the sequence controlling unit 120, thereby collecting the localizer image data (Step S2). For example, the CSF-image collecting unit 133a collects the localizer image data having the imaging area of the entire head of the subject P and displays the localizer image on the display 135, as illustrated in FIG. 2.

After that, the CSF-image collecting unit 133a receives the input of the imaging area R1 and the tagged region R2 on the localizer image displayed on the display 135 at Step S2, and sets the input imaging area R1 and tagged region R2 as the imaging conditions of the imaging scan (Step S3).

Subsequently, the CSF-image collecting unit 133a executes the imaging scan according to the imaging area R1 and the tagged region R2 set at Step S3, and collects the k-space data of the time-series CSF images (Step S4). For example, the CSF-image collecting unit 133a uses pulse sequences such as a balanced steady-state free precession (bSSFP), a fast spin echo (FSE), and a fast asymmetric spin echo (FASE) to execute a three-dimensional scan or a two-dimensional scan.

Figure 6:
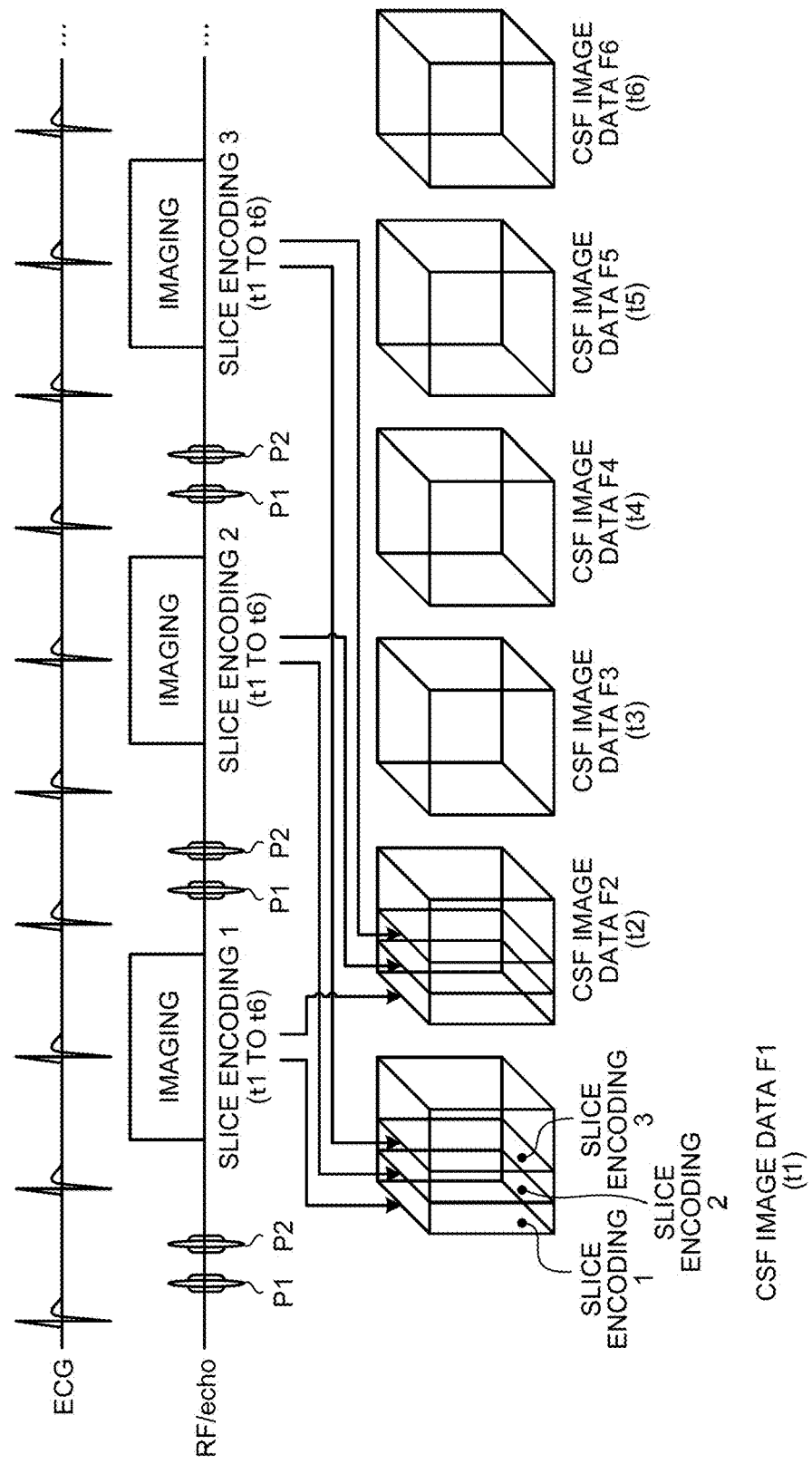
FIG. 6 is a diagram for explaining imaging relating to some embodiments.

FIG. 6 is a diagram for explaining imaging according to the first embodiment. For example, as illustrated in FIG. 6, the CSF-image collecting unit 133a applies the spatial non-selective IR pulse P1 and the spatial-selective IR pulse P2 triggered by the R wave of the ECG signal. After that, the CSF-image collecting unit 133a collects the k-space data for a slice encoding for a plurality of time phases within one TR. For example, the CSF-image collecting unit 133a consecutively collects the k-space data from the time phase t1 to the time phase t6 for a slice encoding within a certain TR. The shorter interval of the time phases increases the time resolution.

The above-described embodiment is provided merely for exemplary purpose and not limiting. The k-space data for a given number of segments is collected for a plurality of time phases. For another example, the k-space data for one time phase are collected within one TR and the k-space data for a plurality of time phases are collected while changing the TI for each TR. In addition, the synchronization used in the embodiment is not limited to the cardiac synchronization and is, for example, the respiratory synchronization, the sphygmic synchronization adopting a peripheral pulse gating (PPG) signal, or the synchronization adopting a clock signal. If the cardiac synchronization, the respiratory synchronization, or the sphygmic synchronization is used, an external device for detecting the ECG signal or the like is coupled to the MRI apparatus 100. The pulse sequence used for the imaging is merely an example and is arbitrarily modified depending on the purpose of the imaging and the form of the operation of images.

As illustrated in FIG. 5, the image generating unit 136 generates the CSF image data and stores the data in the memory unit 132 (Step S5). For example, as illustrated in FIG. 6, the image generating unit 136 combines the k-space data for each slice encoding collected for each TR and executes reconstruction processing on the data, thereby generating the CSF image data for a time phase. As described above, the image generating unit 136 generates the CSF image F1 corresponding to the time phase t1, the CSF image F2 corresponding to the time phase t2, the CSF image F3 corresponding to the time phase t3, the CSF image F4 corresponding to the time phase t4, the CSF image F5 corresponding to the time phase t5, and the CSF image F6 corresponding to the time phase t6, respectively.

Figure 7:
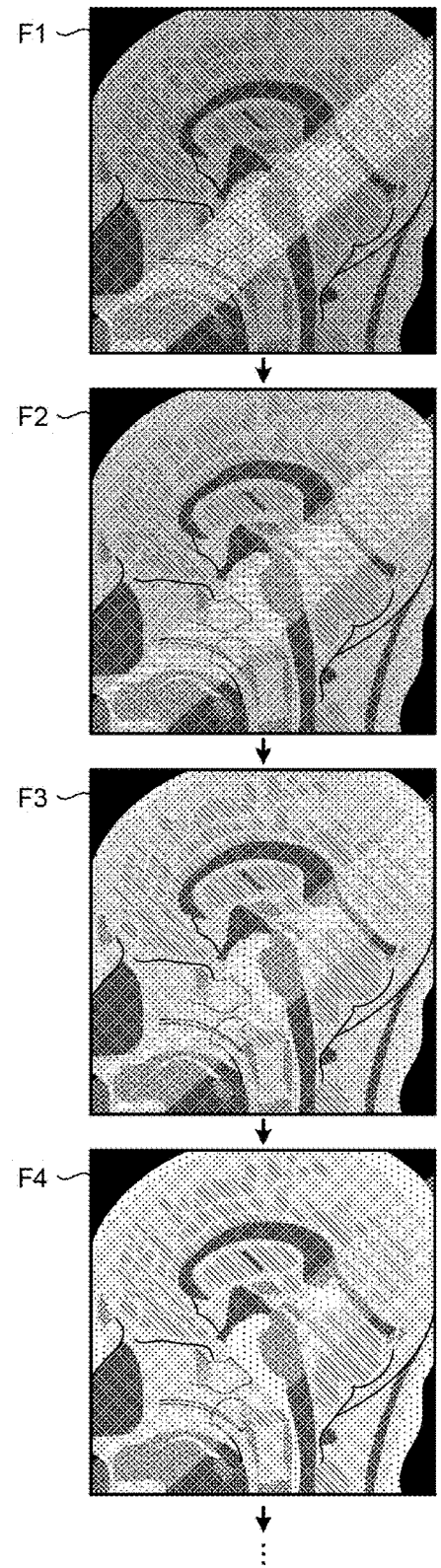
FIG. 7 is a diagram for explaining CSF image data according to the first embodiment.

FIG. 7 is a group of diagrams for explaining the CSF image data according to the first embodiment. In the CSF image, the CSF existing in the brain of the subject P is visualized. For example, it is visualized that the tagged CSF flows out of the cerebral aqueduct and that the CSF without a tag flows into the cerebral aqueduct.

As illustrated in FIG. 7, for example, in the CSF image F1 corresponding to the time phase t1, the signal values in the imaging area R1 are entirely low and the signal values in the tagged region R2 are entirely high, which makes the contrast between the imaging area R1 and the tagged region R2 clear. Those who observe the CSF image F1 therefore can recognize the tagged region R2. Those who observe the CSF image F4 corresponding to the time phase t4, for example, however, can hardly recognize the tagged region R2, as illustrated in FIG. 7, because the contrast between the imaging area R1 and the tagged region R2 gradually decreases. This occurs because the longitudinal magnetization of the tissues within the imaging area R1 relaxes (restores to its original state) as the time elapses.

Subsequently, the CSF-region detecting unit 133b reads from the memory unit 132 the CSF image data. The CSF-region detecting unit 133b then detects the tagged CSF region from the CSF image data (Step S6). As described above with reference to FIG. 3A, the signal value (the longitudinal magnetization) in the tissues within the imaging area R1 contrasts with the signal value (the longitudinal magnetization) in the tissues within the tagged region R2. The CSF-region detecting unit 133b therefore utilizes the contrast to execute threshold processing such as k-means clustering or a discriminant analysis method, thereby detecting the tagged CSF region out of the CSF image data. As illustrated in FIG. 3A, the contrast between the tagged CSF region and other imaging area is likely to decrease as the time elapses. It is therefore useful to switch the parameter for automatic detection (e.g., a threshold) adaptively as the time elapses.

The tagged CSF region may be detected with other methods. For example, the CSF-region detecting unit 133b may detect the CSF region with a segmentation method in which a contour model such as an active contour model (ACM), an active shape model (ASM), and an active appearance model (AAM). For another example, the CSF-region detecting unit 133b may detect the CSF region by using an input by the operator or receiving a specification of the CSF region directly by the operator (e.g., an input of coloring).

Subsequently, the display-image generating unit 133c overlays the positional information of the tagged region R2 and the CSF information on the CSF image, thereby generating the display image data (Step S7). For example, the display-image generating unit 133c reads the positional information of the tagged region R2 from the CSF-image collecting unit 133a and overlays the data generated by coloring the tagged region R2 entirely on the CSF image data read from the memory unit 132. The display-image generating unit 133c receives the CSF information from the CSF-region detecting unit 133b and overlays the color-coded CSF region data based on the positional relation between the CSF region and the tagged region R2 on the CSF image data. As described above, the overlap is achieved by overlaying display image data of a plurality of layers generated by the display controlling unit 133d, or by generating overlaid display image data. Subsequently, the display controlling unit 133d displays the generated image data as described above on the display 135. In the first embodiment, a two-dimensional sagittal image serving as a display image is provided merely for exemplary purpose, but the embodiment is not limited to this image. Alternatively, other cross-sectional images such as a coronal image and an axial image, or a three-dimensional image is used in some embodiments.

Figure 8A:
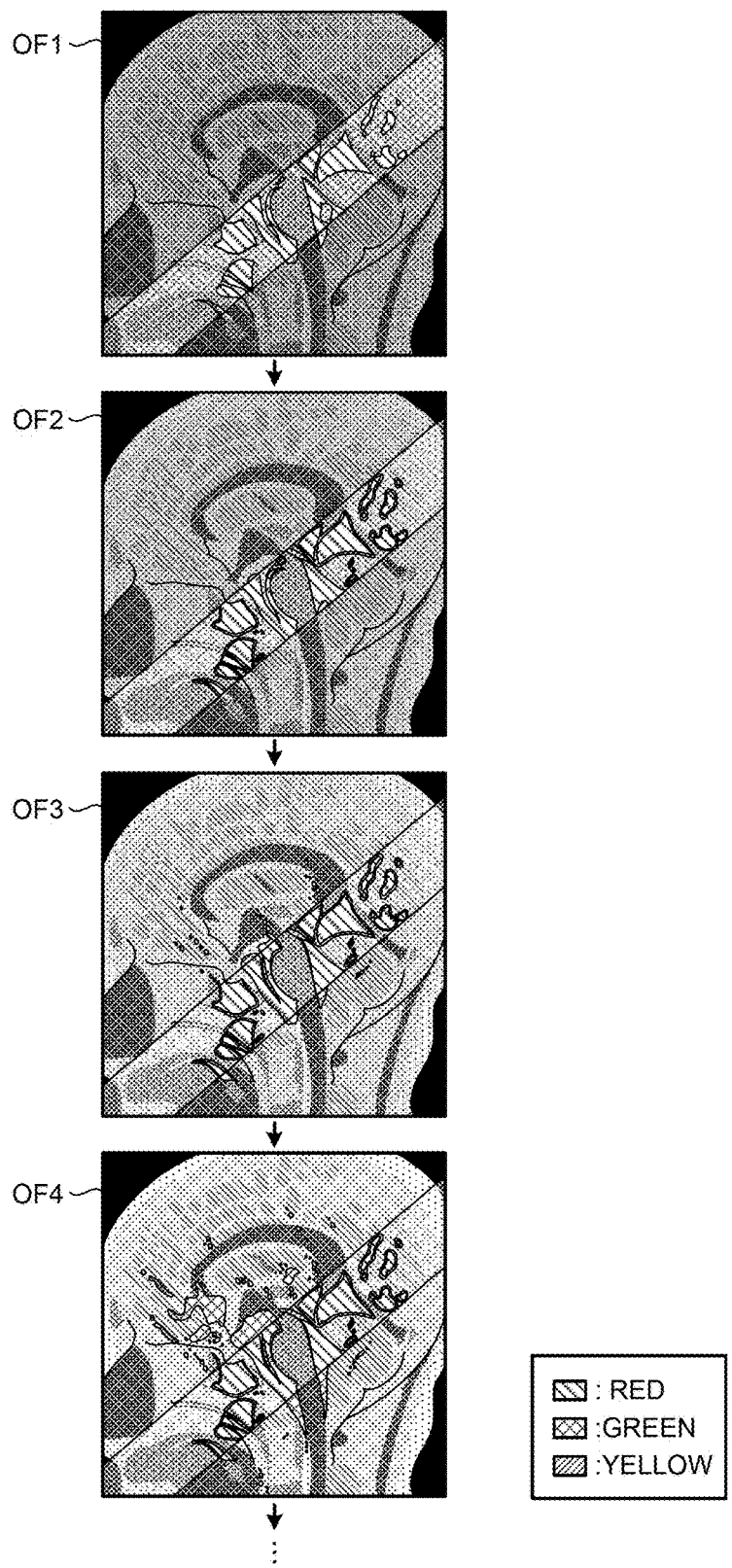
FIG. 8A is a group of diagrams for explaining display images according to the first embodiment.
Figure 8B:
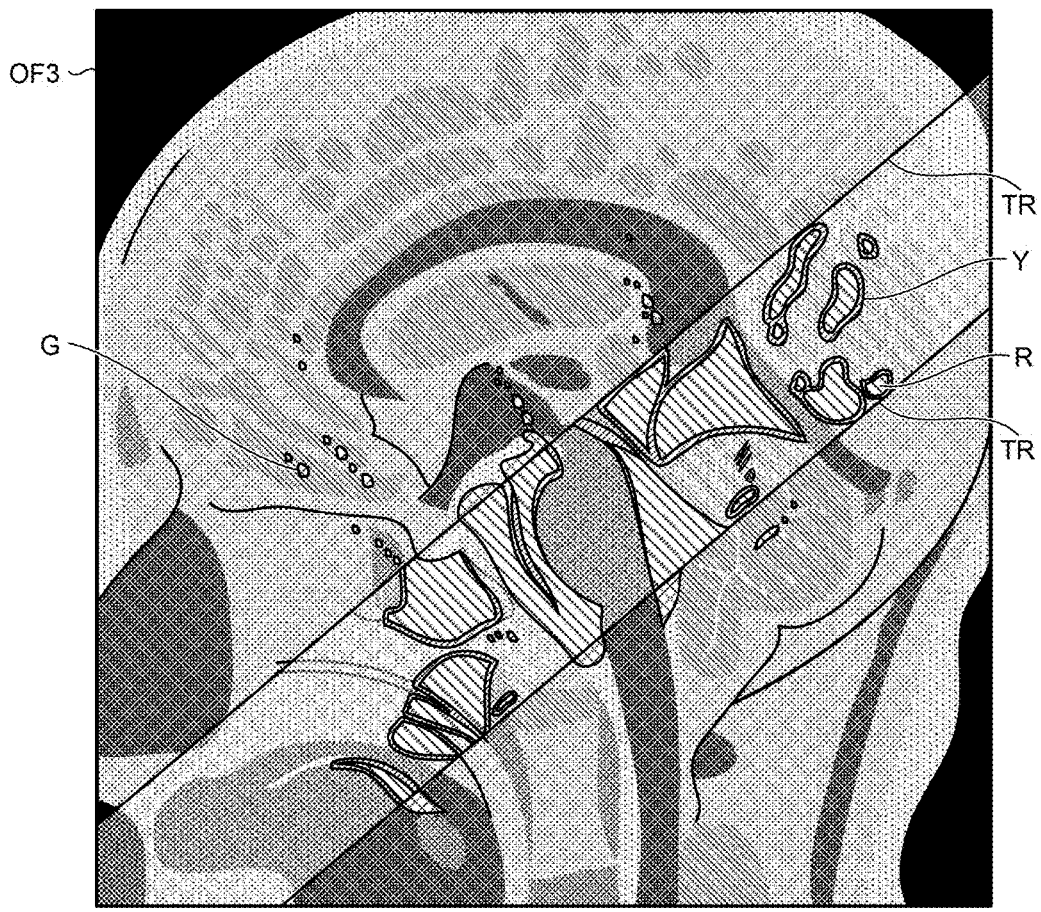
FIG. 8B is a diagram for explaining a display image according to the first embodiment.
Figure 8C:
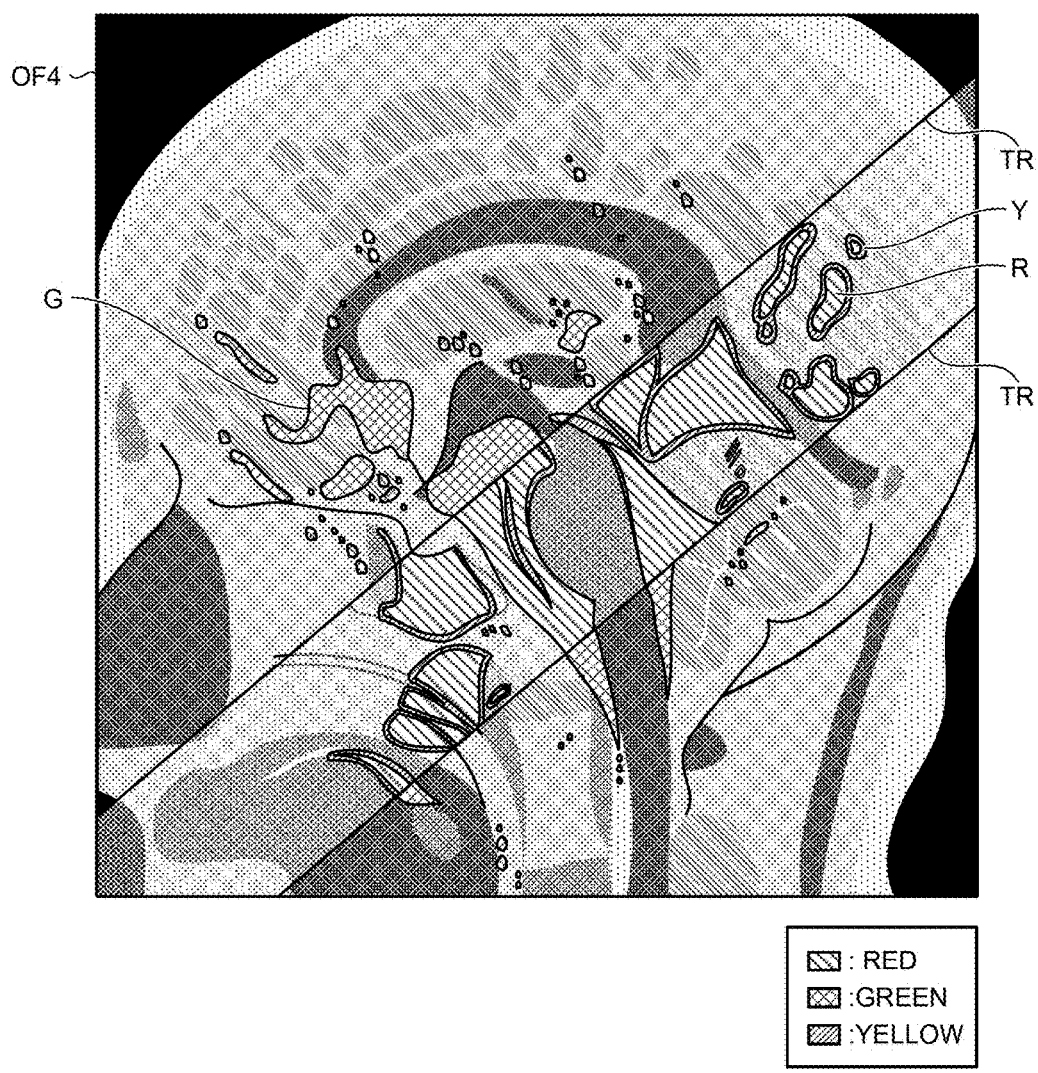
FIG. 8C is a diagram for explaining a display image according to the first embodiment.

FIGS. 8A to 8C are diagrams for explaining display images according to the first embodiment. As illustrated in FIG. 8A, in every display image from the display image OF1 corresponding to the time phase t1 to the display image OF4 corresponding to the time phase t4, the tagged region R2 is highlighted by coloring. Those who observe the display images therefore can always recognize the tagged region R2 regardless of the decrease of the contrast associated with the relaxation (restoration) of the longitudinal magnetization. In addition, in every display image, the CSF region is colored based on the positional relation between itself and the tagged region R2. Those who observe the display images therefore can readily understand the dynamic state of CSF.

These aspects will now be described in detail with reference to FIGS. 8B and 8C. FIG. 8B corresponds to an enlarged view of the display image OF3 illustrated in FIG. 8A and FIG. 8C corresponds to an enlarged view of the display image OF4 illustrated in FIG. 8A. For convenience of description, in FIGS. 8A to 8C, the entire coloring of the tagged region R2 is substituted with representing upper and lower boundary lines of the tagged region R2. For convenience of description, in FIGS. 8A to 8C, the color-coding of the CSF region is substituted with pattern-coding of the CSF region. The corresponding relation between the colors and the patterns is represented in the legends in FIGS. 8A to 8C. The coloring and color-coding according to the embodiment are provided merely for exemplary purpose and not limiting. This is applied to other embodiments.

Firstly, the display-image generating unit 133c, for example, as illustrated in FIG. 8B, overlays the data in which the entire tagged region R2 sandwiched between the boundary lines TR is colored with a light yellow, on the CSF image data. The display-image generating unit 133c, for example, as illustrated in FIG. 8B, overlays the color-coded CSF region data using different colors between inside and outside of the tagged region R2, on the CSF image data.

For example, the display-image generating unit 133c colors in green (G) the CSF region tagged in the tagged region R2 and flowed out from the tagged region R2, and overlays the colored CSF region on the CSF image data. The display-image generating unit 133c colors in red (R) the CSF region tagged in the tagged region R2 and still remains in the tagged region R2, and overlays the colored CSF region on the CSF image data. In addition, the display-image generating unit 133c colors in deep yellow (Y), in time-series frames, the region where a tagged CSF tagged in the tagged region R2 exists in a frame in the past and no tagged CSF exists in the target frame, and overlays the colored CSF region on the CSF image data. That is, the display-image generating unit 133c compares the region detected as a CSF region to the region in its time-series frames. The display-image generating unit 133c then allocates a given display mode to the region having a difference among the frames.

As described above, after receiving the CSF information from the CSF-region detecting unit 133b, the display-image generating unit 133c colors in green (G) the CSF region positioned outside of the tagged region R2. The display-image generating unit 133c colors in red (R) the CSF region positioned inside of the tagged region R2. In addition, the display-image generating unit 133c colors in deep yellow (Y) the region where colored in red (R) in a frame in the past and no CSF region is detected in the target frame. The region in deep yellow (Y) is considered to include other body fluids (e.g., the CSF without a tag) flowing in.

The display image is generated and displayed in this manner, which enables those who observe the display image to readily understand the dynamic state of CSF, as seen in FIG. 8B compared with FIG. 8C. For example, they can readily understand the dynamic state of CSF visually as follows: whether any CSF flows from the third ventricle to the cerebral aqueduct or not; whether any CSF flows in the opposite direction, that is, from the cerebral aqueduct to the third ventricle or not; whether no CSF flows; or whether any CSF goes and comes back between the third ventricle and the cerebral aqueduct.

The display controlling unit 133d sequentially provides the time-series display images on a time-series basis in a cine display. The display controlling unit 133d provides the display images in a loop display by repeating a cine display of the display image in the first time phase coupled to the display image in the last time phase. Alternatively, the display controlling unit 133d provides the display images having a plurality of time phases in a tile display by arranging the display images for some or all of the time phases on the display 135. When providing the display images on a time-series basis in a cine display or in a loop display, the display controlling unit 133d arranges the display images according to the information associated with each frame such as imaging time information, imaging timing information, and a frame number. Alternatively, the display controlling unit 133d appropriately extracts the display images having different time phases out of the time-series display images and provides the extracted display images in a cine display, in a loop display, or in a tile display.

As described above, the dynamic state of CSF can be readily recognized in the first embodiment. The body fluid such as CSF goes and comes back between inside and outside of the tagged region. Those who observe the CSF images therefore have difficulty in understanding whether the tagged CSF flows from the tagged region; or whether the CSF without a tag flows into the tagged region. According to the first embodiment, the tagged CSF region is detected and colored based on the positional relation between the CSF region and the tagged region. The colored CSF region is overlaid on the CSF image. This operation achieves display of flow-out from the tagged region distinguished from the flow-in into the tagged region. This operation also enables those who observe the display image to readily understand the dynamic state of CSF.

According to the first embodiment, the tagged region that has been colored is overlaid on the CSF image. This operation enables those who observe the CSF image to clearly identify the position of the tagged region regardless of the decrease of the contrast associated with the relaxation (restoration) of the longitudinal magnetization.

Modification 1 of the First Embodiment

In the first embodiment, a color-coded tagged region is overlaid on all of the display images included in the display images. This operation is provided merely for exemplary purpose and not limiting. For example, the display-image generating unit 133c switches the overlap/non-overlap of the tagged region with the CSF image in each display image depending on the contrast between the imaging area and the tagged region.

Figure 9:
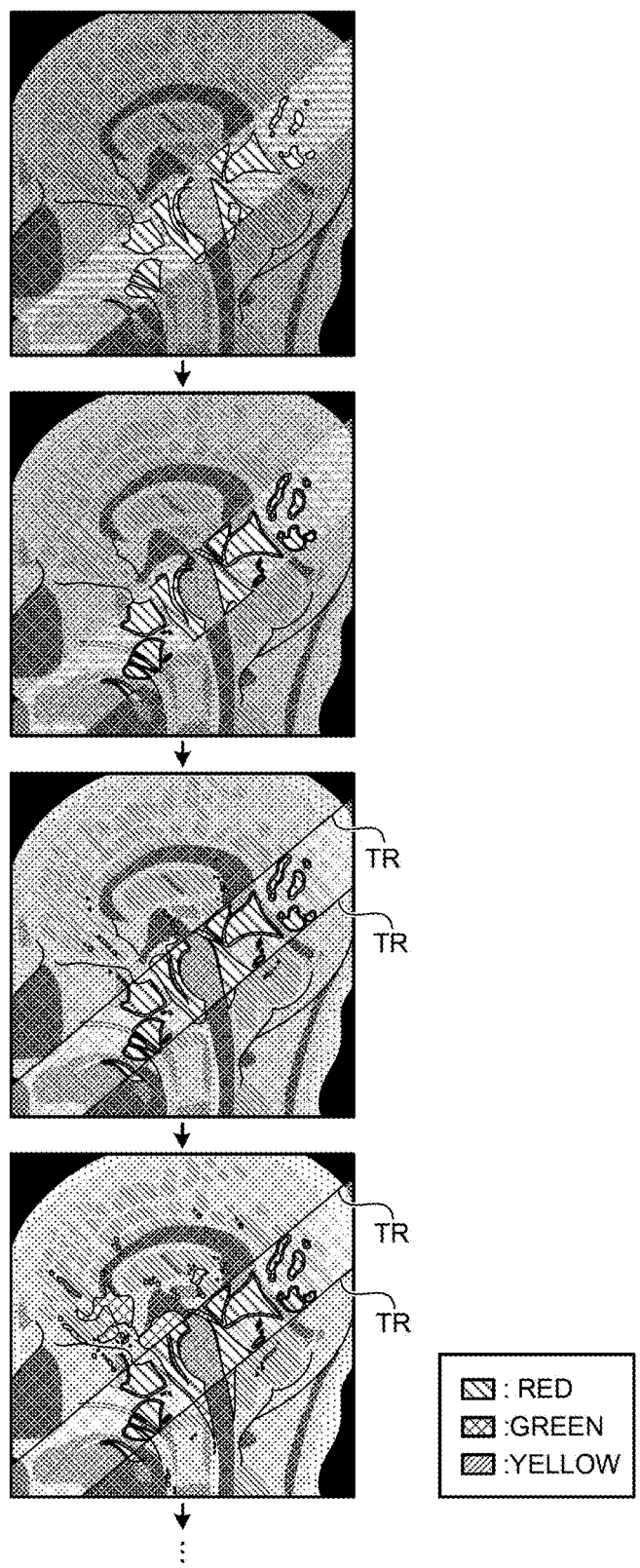
FIG. 9 is a group of diagrams for explaining display images according to a modification of the first embodiment.

FIG. 9 is a group of diagrams for explaining display images according to a modification of the first embodiment. If the contrast between the imaging area R1 and the tagged region R2 is relatively high in the CSF image, the display-image generating unit 133c generates the display image data in which the CSF region alone is overlaid, that is, without the color-coded tagged region R2, for example. If the contrast between the imaging area R1 and the tagged region R2 is relatively low in the CSF image, the display-image generating unit 133c generates the display image data in which the color-coded tagged region R2 and the CSF region are overlaid. The display-image generating unit 133c determines to generate one of these display image data based on a threshold defined relating to the contrast. Alternatively, the display-image generating unit 133c determines to generate one of these display image data based on the time-series order of each display image (e.g., a rule that the first to second frames out of all of the six frames are not overlaid; or an instruction from the operator).

The display-image generating unit 133c changes the density of the tagged region depending on the contrast, for example, rather than switching the overlap/non-overlap of the tagged region. Also in this operation, the display-image generating unit 133c determines to change the density based on a threshold defined relating to the contrast. Alternatively, the display-image generating unit 133c determines to change the density based on the time-series order of each display image.

In addition, the display-image generating unit 133c switches the overlap/non-overlap of the tagged region with the CSF image in each display image according to an instruction input from an operator at any time while the display controlling unit 133d consecutively replays the display images in a cine display or in a loop display, for example. When using the above-described method for generating the display image data by using a plurality of layers, the display-image generating unit 133c generates an underlying layer of the display image without the color-coded tagged region (the CSF image and the CSF region) and a layer of the color-coded tagged region that will be overlaid on the underlying display image. The display controlling unit 133d, for example, displays a button (ON/OFF button) for switching the overlap/non-overlap of the tagged region on the display 135. If an operator inputs an instruction to overlay the tagged region (if the ON button is pressed) while the display controlling unit 133d consecutively replays the display images, the display controlling unit 133d overlays the color-coded tagged region on the underlying display image. For example, at the timing of the ON button being pressed, the display controlling unit 133d generates two layers of the display image in real time, and then overlays them with each other and displays the overlaid image. By contrast, if an instruction not to overlay the color-coded tagged region (if the OFF button is pressed), the display controlling unit 133d cancels the overlap of the color-coded tagged region and simply displays the underlying display image. For example, at the timing of the OFF button being pressed, the display controlling unit 133d generates only the underlying layer of the display image in real time, and then displays the generated image. The layers described above may be defined in another way.

For example, in some embodiments, the display-image generating unit 133c preliminarily generates a series of the time-series display image data (the display image for two layers) and then transmits the series of the display image data at a time to the display controlling unit 133d. The display controlling unit 133d switches the overlap/non-overlap of the layer of the tagged region according to an instruction by the operator.

When using the above-described method for generating the display image data by using an overlaid image, the display-image generating unit 133c generates the display image without the color-coded tagged region (the display image for the OFF); and the display image where the color-coded tagged region is overlaid (the display image for the ON). If an operator inputs an instruction to overlap the tagged region (if the ON button is pressed) while the display images are consecutively replayed, the display-image generating unit 133c generates the display image for the ON in real time. Subsequently, the display controlling unit 133d displays the generated image. By contrast, if an instruction not to overlay the tagged region (if the OFF button is pressed), the display-image generating unit 133c generates the display image for the OFF in real time. Subsequently, the display controlling unit 133d displays the generated image. If the operator switches the overlap/non-overlap of the tagged region and also changes the display contrast setting, for example, the change can be thus reflected on the consecutive replay of the display images.

For example, in some embodiments, the display-image generating unit 133c preliminarily generates a series of the time-series display image data (the display image for the OFF and the display image for the ON) and then transmit the series of the display image data at a time to the display controlling unit 133d. The display controlling unit 133d displays on the display 135 either one of the display image for the OFF and the display image for the ON according to the instruction by the operator.

Modification 2 of the First Embodiment

In the first embodiment, the CSF region is classified by using different colors inside of the tagged region and outside of the tagged region, and the color-coded CSF region is overlaid on the CSF image. This method is provided merely for exemplary purpose and not limiting. The display-image generating unit 133c combines color-coding based on signal values with the color-coding based on the positional relation between the CSF region and the tagged region. For example, the display-image generating unit 133c prepares a color correspondence table that defines the corresponding relation between signal values and a color table for inside of the tagged region and outside of the tagged region, respectively. According to the color correspondence table, the display-image generating unit 133c colors the CSF region positioned outside of the tagged region R2 based on the signal values in colors gradually changing from blue to green, and then overlays the colored CSF region on the CSF image data, for example. The display-image generating unit 133c colors the CSF region positioned inside of the tagged region R2 based on the signal values in colors gradually changing from yellow to magenta, and then overlays the colored CSF region on the CSF image data.

The display-image generating unit 133c also allocates colors according to a color correspondence table including different ranges depending on the time phases in a time-series. That is, the display-image generating unit 133c changes the range of the above-described color correspondence table as the time elapses. As described above, the contrast between the tagged CSF region and other imaging area is likely to decrease as the time elapses. If the colors gradually changing from blue to red are allocated corresponding to the signal values "0" to "100", for example, at the time of high contrast, and after the time elapses, the relaxation of the longitudinal magnetization turns the entire region to red at the time of low contrast. To cope with this, the display-image generating unit 133c changes the range of the color correspondence table. Specifically, at the time of low contrast, the colors gradually changing from blue to red are allocated corresponding to the signal values "50" to "100", for example.

For another example, the display-image generating unit 133c colors the CSF region according to the feature amount such as the area and the surface area of the CSF region segmented relative to inside/outside of the tagged region, rather than classifying the CSF region by using different colors inside of the tagged region and outside of the tagged region. Specifically, the display-image generating unit 133c allocates a red color to the CSF region having a relative large area of the CSF flowed from the tagged region R2. By contrast, the display-image generating unit 133c allocates a green color to the CSF region having a relative small area of the CSF flowed from the tagged region R2. On this occasion, the display-image generating unit 133c receives a specification of the target region for coloring from the operator. For example, the operator selects the CSF region where the CSF flows from the tagged region R2, the CSF region where the CSF still remains in the tagged region R2, or other body fluids (e.g., the CSF without a tag) flowed into the tagged region. The display-image generating unit 133c then allocates a color to the region specified by the operator based on the threshold of the feature amount defined in advance. This operation is useful because only a particular portion that the observer desires to observe can be colored.

In the first embodiment, the entire tagged region is colored to clearly represent the tagged region. This operation is provided merely for exemplary purpose and not limiting. For example, the display-image generating unit 133c colors an area outside of the tagged region, rather than coloring the tagged region. For another example, the display-image generating unit 133c simply represents a boundary line surrounding the tagged region rather than coloring the tagged region.

Second Embodiment

The following describes a second embodiment. In the first embodiment, the CSF region is overlaid on the CSF image in the display mode based on the positional relation between the CSF region and the tagged region. For example, the CSF region is classified by using different colors inside of the tagged region and outside of the tagged region. The above-described embodiment is provided merely for exemplary purpose and not limiting. In the second embodiment, the display-image generating unit 133c overlays an arbitrary boundary line unrelated to the tagged region on the CSF image. The display-image generating unit 133c also overlays the CSF region using the display mode based on the positional relation between the CSF region and the arbitrary boundary line. The display-image generating unit 133c generates the display image data and the display controlling unit 133d displays the images in the same manner as in the above-described embodiment. The overlapped explanation thereof will be therefore omitted.

Figure 10A:
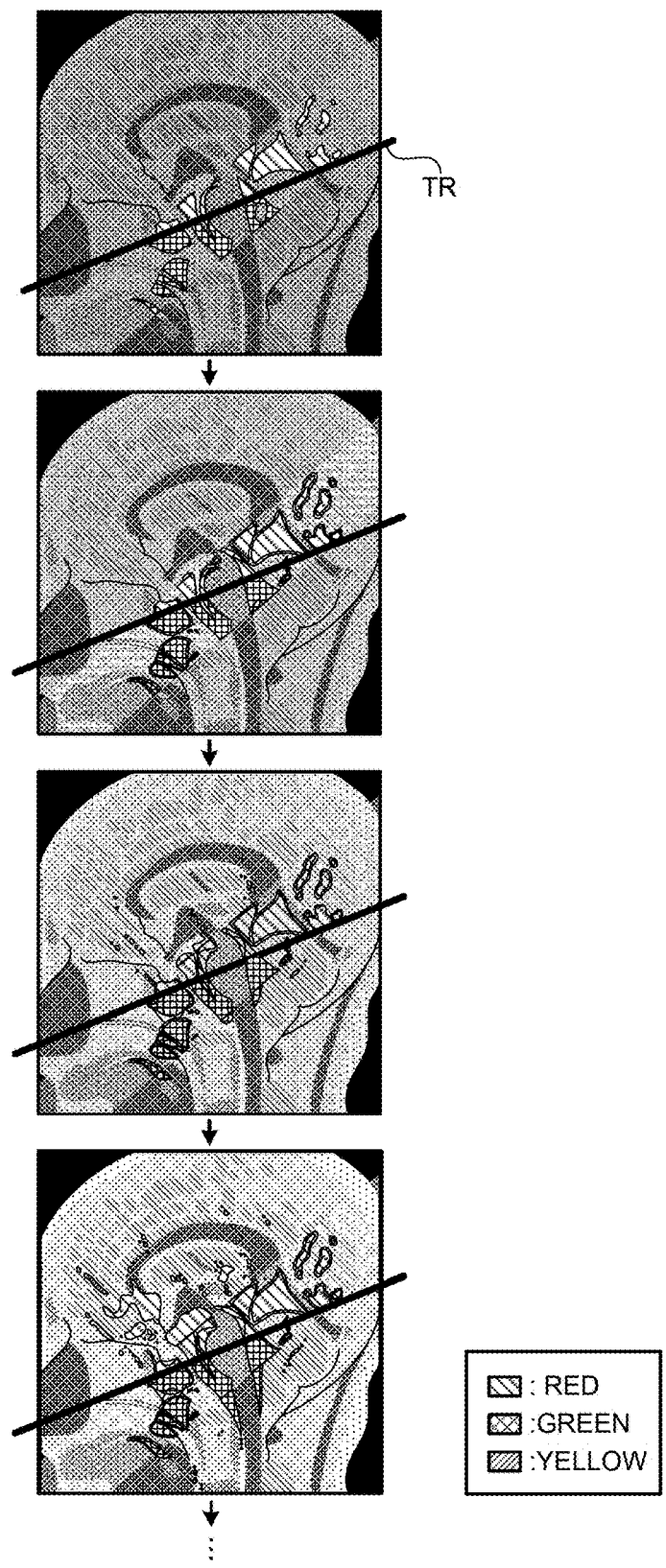
FIG. 10A is a group of diagrams for explaining display images according to a second embodiment.
Figure 10B:
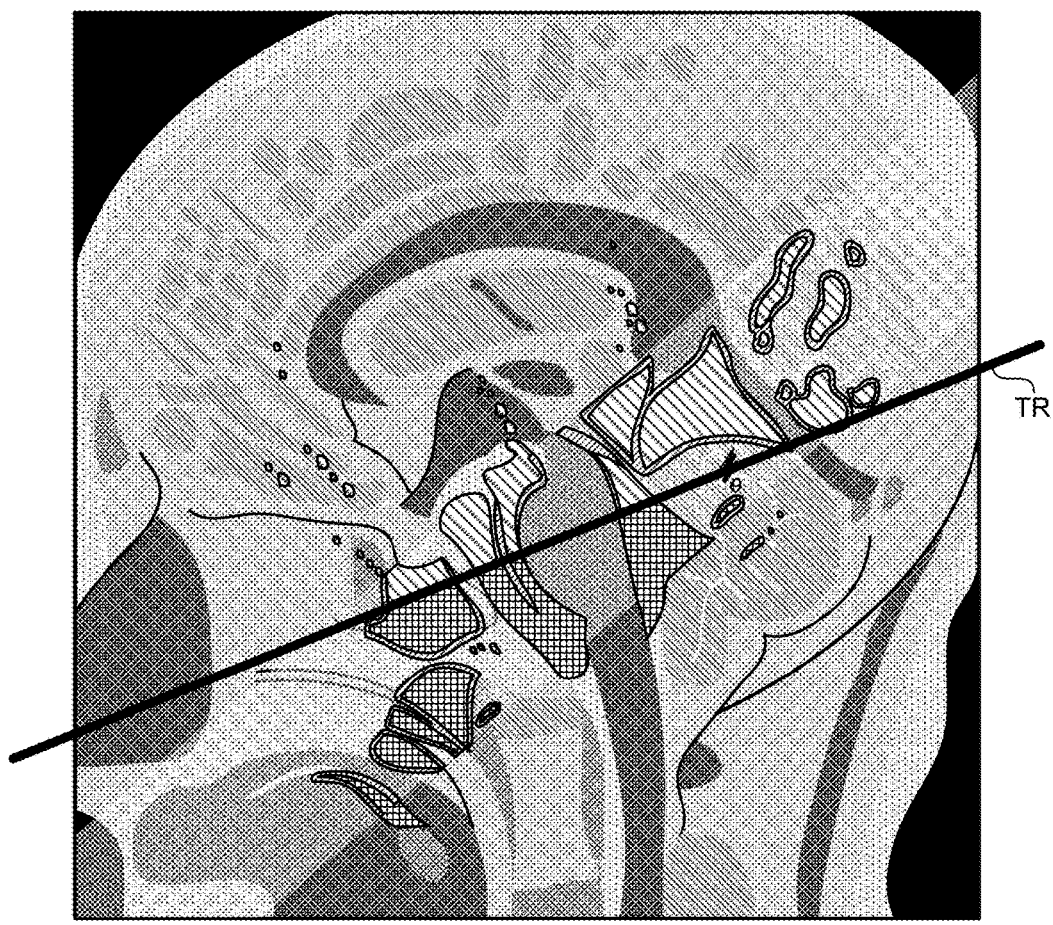
FIG. 10B is a diagram for explaining a display image according to the second embodiment.
Figure 10C:
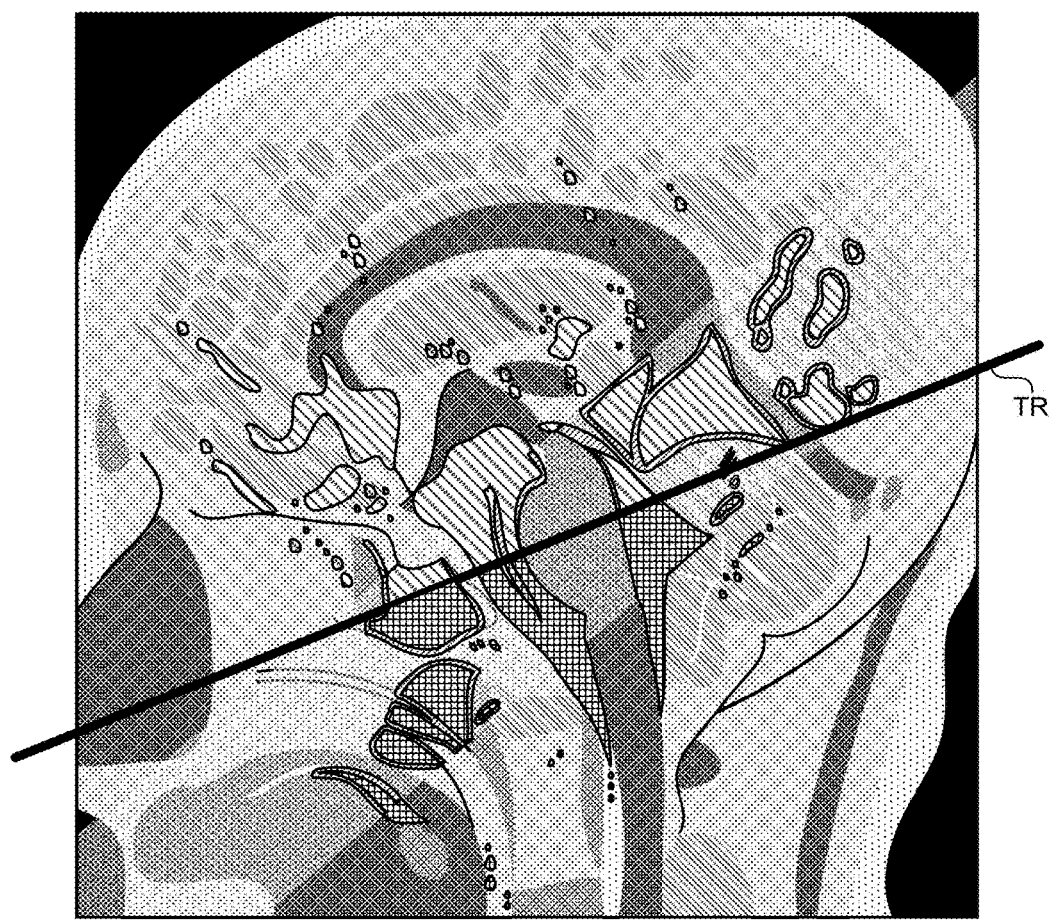
FIG. 10C is a diagram for explaining a display image according to the second embodiment.

FIGS. 10A to 10C are diagrams for explaining display images according to the second embodiment. As illustrated in FIG. 10A, the display-image generating unit 133c overlays a boundary line TR on every display image. The display-image generating unit 133c classifies the CSF region by using different colors between the area higher than the boundary line TR and the area lower than boundary line TR in every display image. The display-image generating unit 133c then overlays the colored CSF region on the CSF image. The display-image generating unit 133c defines the boundary line TR by receiving an input from the operator. The display-image generating unit 133c also defines the boundary line TR automatically based on the positional relation related to the tagged region R2. Specifically, the display-image generating unit 133c defines the boundary line by automatically calculating the boundary line passing through the center point of the tagged region R2. If the boundary line is defined by receiving an input by the operator, the operator can appropriately define the boundary line on an arbitrary position where the operator desires to observe the dynamic state of CSF.

These aspects will now be described in detail with reference to FIGS. 10B and 10C. FIG. 10B corresponds to an enlarged view of the display image at time phase t3 (the third from the top) illustrated in FIG. 10A, and FIG. 10C corresponds to an enlarged view of the display image at time phase t4 (the fourth from the top) illustrated in FIG. 10A.

Firstly, the display-image generating unit 133c, for example, as illustrated in FIG. 10B, overlays a thick boundary line TR on the CSF image data. The display-image generating unit 133c, for example, as illustrated in FIG. 10B, classifies the CSF region by using different colors between the area higher than the boundary line TR and the area lower than the boundary line TR. The display-image generating unit 133c then overlays the colored CSF region on the CSF image.

For example, the display-image generating unit 133c colors in green (G) the CSF region tagged in the tagged region R2 and positioned lower than the boundary line TR, and overlays the colored CSF region on the CSF image data. The display-image generating unit 133c colors in red (R) the CSF region tagged in the tagged region R2 and positioned higher than the boundary line TR, and overlays the colored CSF region on the CSF image data. In addition, the display-image generating unit 133c colors in yellow (Y) the region where CSF tagged in the tagged region R2 exists in a frame in the past and no tagged CSF exists in the target frame, and overlays the colored CSF region on the CSF image data.

The display controlling unit 133d sequentially provides the time-series display images on a time-series basis in a cine display. The display controlling unit 133d also provides the display images having a plurality of time phases in a tile display by arranging the display images for some or all of the time phases on the display 135. Alternatively, the display controlling unit 133d extracts the display images having different time phases out of the time-series display images and provides the extracted display images in a cine display or in a tile display.

In the second embodiment, one boundary line is overlaid on the display image. This operation is provided merely for exemplary purpose and not limiting. A plurality of boundary lines are overlaid on the display image. For example, the display-image generating unit 133c may overlap a plurality of boundary lines with the CSF image in parallel with the boundary line illustrated in FIG. 10A. The display-image generating unit 133c then classifies the CSF region by using different colors on the sections divided by the boundary lines. Specifically, the display-image generating unit 133c allocates a red color to the CSF region between the first boundary line and the second boundary line, a yellow color to the CSF region between the second and the third boundary lines, and a green color to the CSF region between the third and the fourth boundary lines, for example. This operation achieves a color-coding on the CSF region flowed from the tagged region R2 according to the distance of flow, for example.

Also in the display image described in the second embodiment, the overlap/non-overlap of the boundary line unrelated to the tagged region is switched or the density is changed in the same manner as in the first embodiment. Also in the same manner as in the first embodiment, the overlap/non-overlap of the boundary line is switched according to an instruction input from the operator at any time while the display images are consecutively replayed in a cine display or in a loop display, for example. Also in the same manner as in the first embodiment, a color-coding based on signal values are combined; the range of the above-described color correspondence table is changed as the time elapses; and the CSF region is classified according to the feature amount such as the area and the surface area of the CSF region by using different colors between the area higher and lower than the boundary line. The boundary line is represented in another way such as coloring an area divided by the boundary line and overlaying the colored area on the image, rather than simply representing the boundary line itself.

Third Embodiment

The following describes a third embodiment. In the first embodiment, the MRI apparatus 100 generates the display image and controls the display. The above-described embodiment is provided merely for exemplary purpose and not limiting. For example, if a piece of information required for later processing, such as the positional information of the tagged region, is associated on the CSF image data, not only the MRI apparatus 100 but also any image processing apparatus is capable of generating the display image and controlling the display. Examples of the image processing apparatus include a workstation, an image storage apparatus (an image server) and a viewer of a picture archiving and communication system (PACS), and an electronic medical recoding system.

Figure 11:
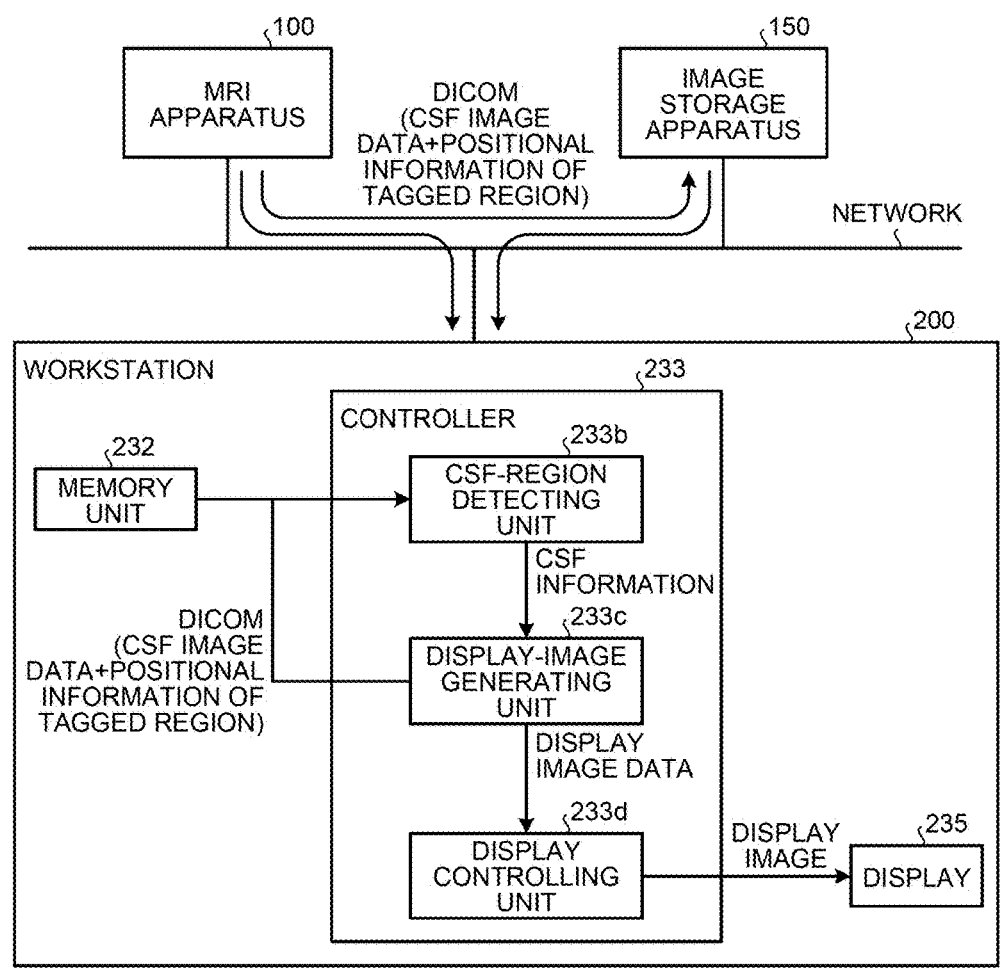
FIG. 11 is a block diagram illustrating the configuration according to a third embodiment.

FIG. 11 is a block diagram illustrating the configuration according to the third embodiment. In the third embodiment, the MRI apparatus 100 includes the CSF-image collecting unit 133a and collects the k-space data of the time-series CSF images. The MRI apparatus 100 also includes the image generating unit 136 that executes reconstruction processing on the k-space data collected by the CSF-image collecting unit 133a, thereby generating the CSF image data.

The CSF image data collected and generated by the MRI apparatus 100 are then stored, for example, in an image storage apparatus 150 in the data structure according to the digital imaging and communications in medicine (DICOM) standards, or transmitted to a workstation 200, a viewer, or other image processing apparatuses. Storing various types of information in the associated information of the DICOM standards (e.g., a private tag) associates the various types of information with the CSF image data, which is useful for later processing. For example, the information associated with the CSF image data indicates that a series of CSF image data are collected on a time-series basis (i.e., the CSF image data can be handled as a moving image). The positional information of the tagged region may also be associated with the CSF image data as the associated information.

The following describes the workstation 200 as an example of the image processing apparatus. In the third embodiment the workstation 200 includes a memory unit 232, a controlling unit 233, and a display 235. The controlling unit 233 includes a CSF-region detecting unit 233b, a display-image generating unit 233c, and a display controlling unit 233d. These components each have the same functions as the CSF-region detecting unit 133b, the display-image generating unit 133c, and the display controlling unit 133d in the above-described embodiments, respectively.

The workstation 200 receives the CSF image data associated with the positional information of the tagged region directly from the MRI apparatus 100 or through the image storage apparatus 150. The workstation 200 then stores the received data in the memory unit 232. After that, in the same manner as the computer 130 in the first embodiment, the workstation 200 reads from the memory unit 232 the CSF image data and the positional information of the tagged region, detects the CSF region, generates the display image, and displays the generated display image.

The configuration illustrated in FIG. 11 is merely an example. For example, the workstation 200 receives the k-space data before reconstruction processing rather than the CSF image data. In addition, a private data structure is used rather than data structure according to the DICOM standards.

Other Embodiments

Embodiments are not limited to the embodiments described above.

In the above-described embodiments, the CSF region and the tagged region are both colored and overlaid on the CSF image. This operation is provided merely for exemplary purpose and not limiting. For example, the display-image generating unit 133c generates display image data with which the tagged region alone is overlaid, that is, without the CSF region. This operation enables those who observe the CSF image to clearly identify the position of the tagged region regardless of the decrease of the contrast between the imaging area and the tagged region associated with the relaxation (restoration) of the longitudinal magnetization. On this occasion, the display-image generating unit 133c overlaps the tagged region with some of the display images selectively, rather than all of the display images. Specifically, the display-image generating unit 133c switches the overlap/non-overlap of the tagged region with the display image depending on the degree of the contrast between the imaging area and the tagged region, or based on the time-series order of the display image. The display-image generating unit 133c generates the display image data and the display controlling unit 133d displays the images in the same manner as in the above-described embodiments.

Figure 12:
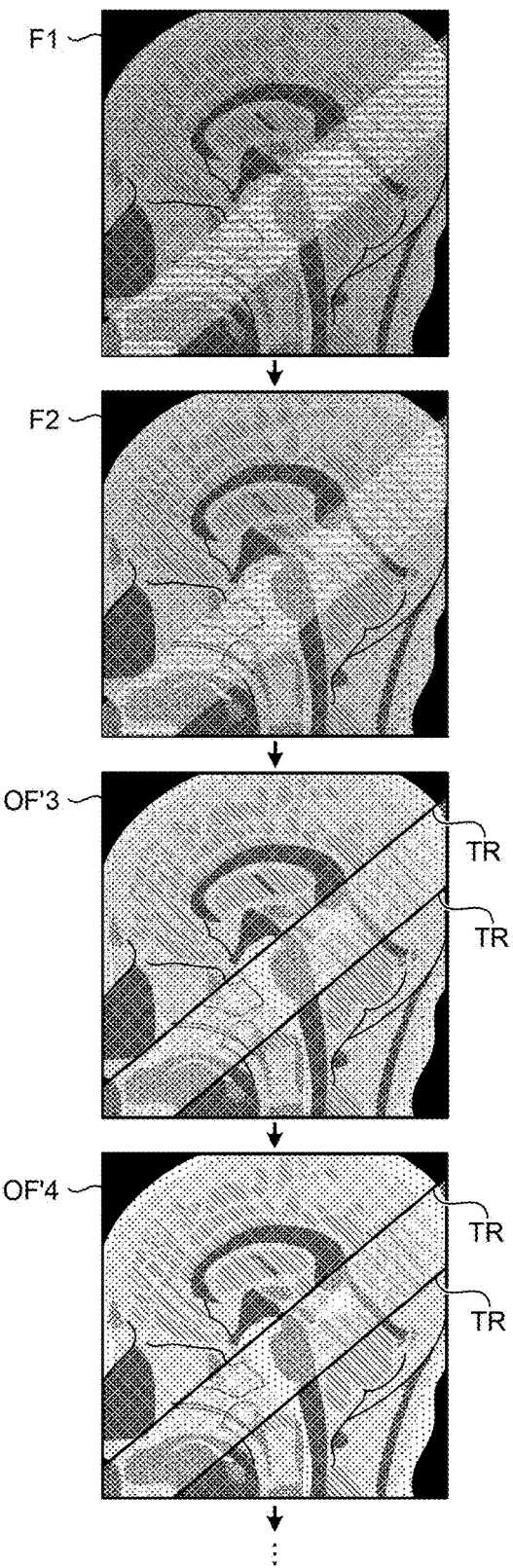
FIG. 12 is a group of diagrams for explaining display images according to another embodiment.

FIG. 12 is a group of diagrams for explaining display images according to another embodiment. If the contrast between the imaging area R1 and the tagged region R2 is relatively high in the CSF image, the display-image generating unit 133c generates the display image data without the tagged region R2 overlaid (or the CSF image itself), for example. If the contrast between the imaging area R1 and the tagged region R2 is relatively low in the CSF image, the display-image generating unit 133c generates the display image data with which the tagged region R2 is overlaid. The display-image generating unit 133c determines to generate one of these display image data based on a threshold defined relating to the contrast. Alternatively, the display-image generating unit 133c determines to generate one of these display image data based on the time-series order of each display image (e.g., a rule that the first to second frames out of all of the six frames are not overlaid; or an instruction from the operator).

In the same manner as in the first embodiment, the display controlling unit 133d switches the overlap/non-overlap of the tagged region according to an instruction input from an operator at any time while the display images are consecutively replayed in a cine display or in a loop display, for example.

In the above-described embodiments, the tagged region and the CSF region are colored and overlaid on the CSF image. In the overlaying method, the original image is seen through the color-coded tagged region and the CSF region depending on the defined transmittance of the image. The above-described embodiment is provided merely for exemplary purpose and not limiting. For example, the display-image generating unit 133c clearly represents the tagged region and the CSF region by executing image processing on the CSF image serving as the original image. Specifically, the display-image generating unit 133c executes image processing on the pixels within the imaging area having signal values gradually increased associated with the restoration of the longitudinal magnetization, thereby reducing the signal values for adjustment to maintain the contrast.

In the above-described embodiments, the target part for observation is the third ventricle and the cerebral aqueduct in the brain. These are provided merely for exemplary purpose and not limiting. The spinal cord, the heart, the kidney, and other parts are the observation targets. In the above-described embodiments, the CSF exemplifies the body fluid. This is also provided merely for exemplary purpose and not limiting. The embodiments can be applied to the blood, the lymph, the pancreatic juice, and other body fluids, in the same manner.

In the first embodiment, one tagged region is defined in the imaging area. This configuration is also provided merely for exemplary purpose and not limiting. Alternatively, a plurality of tagged regions are defined in the imaging area. Assuming that a plurality of tagged regions are defined in the imaging area, two tagged regions are disposed in a crossed manner, for example. On this occasion, if the IR pulse is applied to the two tagged regions at or nearly at the same time, the longitudinal magnetization only in the tissues within the crossed and overlapped region inverts twice, that is, returns to the initial state. Specifically, the display-image generating unit 133c distinguishes between one of the two tagged regions and the overlapped region. The display-image generating unit 133c determines the display mode in the region of the body fluid based on the positional relation between the body fluid region and the respective distinguished regions. For example, the display-image generating unit 133c classifies the body fluid region by using different colors on the respective tagged regions and the overlapped region. Assume that a plurality of tagged regions are defined in the imaging area, whereby tagged regions are disposed in a parallel manner, for example. Specifically, the display-image generating unit 133c determines the display mode in the region of the body fluid based on the positional relation between the body fluid region and the respective tagged regions. For example, the display-image generating unit 133c classifies the body fluid region by using different colors on the respective tagged regions.

In the above-described embodiments, the time-series CSF images are assumed to be used. For example, the display controlling unit 133d displays the display images each corresponding to the time-series CSF images. Specifically, the display controlling unit 133d sequentially provides the display images on a time-series basis in a cine display. The display controlling unit 133d also provides the display images in a loop display by repeating a cine display, or in a tile display by arranging the display images having a plurality of time phases. Alternatively, the display controlling unit 133d extracts the display images having different time phases out of the display images on a time-series basis and provides the extracted display images in a cine display, in a loop display, or in a tile display. The above-described embodiments are provided merely for exemplary purpose and not limiting. The targeted CSF images and the display images are not limited to time-series images.

The CSF typically has a complicated dynamic state even in a normal brain. Specifically, the CSF flows in various directions such as in a direction from the lateral ventricle to the third ventricles, and in a direction from the third and fourth ventricles to the lateral ventricle. This feature allows the display controlling unit 133d not to necessarily display the display images on a time-series basis although the CSF images are collected on a time-series basis. That is, the display controlling unit 133d sorts the display images in a particular order according to the feature amount obtained by analyzing the CSF images. The display controlling unit 133d then provides the display images sorted in the order in a sequential display, in a loop display, or in a tile display. Specifically, the display controlling unit 133d calculates the distance between the tagged region and the tip end position of the CSF region flowed from the tagged region. The display controlling unit 133d sorts the display images in the order according to the calculated distance. The display controlling unit 133d then provides the display images sorted in the order in a sequential display, in a loop display, or in a tile display. Alternatively, the display controlling unit 133d calculates the area of the CSF region. The display controlling unit 133d sorts the display images in the order according to the calculated area. The display controlling unit 133d then provides the display images sorted in the order in a sequential display, in a loop display, or in a tile display.

In the embodiments the CSF images are not collected on a time-series basis. After a plurality of CSF images are collected in any method, the display controlling unit 133d sorts the display images in a particular order according to the feature amount obtained by analyzing the CSF images. The display controlling unit 133d then provides the display images sorted in the order in a sequential display, in a loop display, or in a tile display.

Specific Values and Order of Processes

The specific values and the order of processes in above-described embodiments are provided merely for exemplary purpose and not limiting in principle. For example, the pattern of the color-coding and the number of time phases is arbitrarily modified. The order of processes also is arbitrarily modified. Specifically, another preliminary scanning processing is executed in any order. The specific pulse sequence is also arbitrarily modified.

Computer Program

The instructions in the processing procedures according to the above-described embodiments are, for example, executed based on a computer program that is software. A general purpose computer system stores in advance and reads the computer program, thereby achieving advantageous effects similar to the effects achieved by the MRI apparatus 100. The instructions described in the above embodiments are recorded, as a computer program that can be executed by a computer, on a magnetic disk (e.g., a flexible disk, a hard disk), an optical disk (e.g., a CD-ROM, a CD-R, a CD-RW, a DVD-ROM, a DVD±R, a DVD±RW), in a semiconductor memory, or in a recording medium similar thereto. Any format may be used for a recording medium readable by the computer or an embedded system. The computer reads the computer program from the recording medium and causes the CPU to implement the instructions described in the computer program based on the computer program. This achieves the same operation as the MRI apparatus 100 according to the embodiments. The computer reads or loads the computer program via a network.

Furthermore, some of the above-described processes to achieve the embodiments are executed by the operating system (OS) running on the computer based on the computer program installed from the recording medium in a computer or an embedded system, or middleware such as database management software and a network. Furthermore, the recording medium is not limited to those media independent from a computer or an embedded system. Those media may be used that store or temporally store a computer program downloaded over a local area network (LAN) or the Internet, for example. The number of recording media is not limited to one. A plurality of recording media may be used for executing the processes according to the above-described embodiments. That is, one or more recording media may be configured in the embodiments.

The computer or the embedded system in the embodiments executes the processes according to the above-described embodiments, based on the computer program stored in the recording medium. The computer or the embedded system may be a single apparatus such as a personal computer and a microcomputer. Alternatively, the computer or the embedded system is a system in which a plurality of devices are coupled to each other through a network. The computer in the embodiments is not limited to a personal computer and it may include a processor and a microcomputer included in an information processing device. That is, the computer in the embodiments is a general term for devices and apparatuses capable of achieving the functions according to the embodiments through the computer program.

According to the image processing apparatus and the magnetic resonance imaging apparatus in at least one of the embodiments described above, the dynamic state of body fluid can be readily recognized.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. Magnetic resonance image (MRI) processing apparatus comprising:
   MRI processing circuitry configured to
     detect a region of body fluid flowing in a subject and said region having been tagged from a time-series of MR images acquired by MRI scanning an imaging area including a tagged region to which a tagging pulse is applied and MR imaging the imaging area;
     generate a plurality of display MR images in which the detected region of the tagged body fluid is maintained upon a display and remains displayed in different display modes according to a positional relation between the region of the tagged body fluid and a boundary line set in the tagged region; and
     output a time-series of display MR images including the generated plurality of display MR images being displayed on the display.

2. Magnetic resonance image (MRI) processing apparatus comprising:
   MRI processing circuitry configured to
     detect a region of body fluid flowing in a subject and said region having been tagged from a time-series of MR images acquired by MRI scanning an imaging area including a tagged region to which a tagging pulse is applied and MR imaging the imaging area;
     generate a plurality of display MR images in which the detected region of the tagged body fluid is maintained upon a display and remains displayed in different display modes according to whether the region of the tagged body fluid is inside or outside of the tagged region; and
     output a time-series of display MR images including the generated plurality of display MR images being displayed on the display.

3. The apparatus according to claim 1, wherein the MRI processing circuitry is configured to compare regions each detected as a region of the body fluid between the time-series MR images and apply a predetermined display mode to a difference of the MR images between the compared regions.

4. The apparatus according to claim 1, wherein the MRI processing circuitry is configured to determine a region that has been detected as a region of the tagged body fluid in a past MR image and is not detected as a region of the tagged body fluid in a target MR image, and apply a predetermined display mode to the determined region.

5. The apparatus according to claim 2, wherein the MRI processing circuitry is configured to acquire positional information of the tagged region from MR imaging conditions.

6. The apparatus according to claim 2, wherein the MRI processing circuitry is configured to generate, as the plurality of display MR images, MR images in which the region of the tagged body fluid is overlaid on each MR image with color-coding based on whether the region of the tagged body fluid is inside or outside of the tagged region.

7. The apparatus according to claim 6, wherein the MRI processing circuitry is configured to generate, as the plurality of display MR images, MR images in which the region of the tagged body fluid is overlaid on each MR image with color-coding based on whether the region of the tagged body fluid is inside or outside of the tagged region and depending on a signal value in the region of the tagged body fluid.

8. The apparatus according to claim 7, wherein the MRI processing circuitry is configured to apply the color-coding according to a color correspondence table that defines a corresponding relation between an MR signal value and a color and that has different ranges depending on time phases in a time-series.

9. The apparatus according to claim 1, wherein the MRI processing circuitry is configured to generate, as the plurality of display MR images, MR images in which information of the tagged region is overlaid on each MR image.

10. The apparatus according to claim 9, wherein the MRI processing circuitry is configured to change density of the tagged region overlaid on each MR image based on time phases in a time-series.

11. The apparatus according to claim 1, wherein the tagged body fluid is cerebrospinal fluid.

12. A magnetic resonance image (MRI) apparatus comprising:
   an MRI system configured to collect a time-series of magnetic resonance (MR) images acquired by applying a tagged pulse to a tagged region in an imaging area and imaging the imaging area;
   a display; and
   MRI processing circuitry configured to
     detect a region of body fluid flowing in a subject and said region having been tagged from the time-series of MR images;
     generate a plurality of display MR images in which the detected region of the tagged body fluid is maintained upon a display and remains displayed in different display modes according to a positional relation between the region of the tagged body fluid and a boundary line, set in the tagged region; and
     output a time-series of display MR images including the generated plurality of display MR images being displayed on the display.

13. A magnetic resonance image (MRI) processing method comprising:
- detecting a region of body fluid flowing in a subject and said region having been tagged from a time-series of MR images acquired by MRI scanning an imaging area including a tagged region to which a tagging pulse is applied and MR imaging the imaging area;
- generate a plurality of display MR images in which the detected region of the tagged body fluid is maintained upon a display and remains displayed in different display modes according to a positional relation between the region of the tagged body fluid and a boundary line, set in the tagged region; and
- outputting a time-series of display MR images including the generated plurality of display MR images being displayed on the display.

14. A magnetic resonance image (MRI) processing apparatus comprising:
- an MRI processor; and
- a memory that stores processor-executable instructions that, when executed by the MRI processor, cause the MRI processor to:
  - detect a region of body fluid flowing in a subject and said region having been tagged from a time-series of images acquired by MRI scanning an imaging area including a tagged region to which a tagging pulse is applied and MR imaging the imaging area;
  - generate a plurality of display MR images in which the detected region of the tagged body fluid is maintained upon a display and remains displayed in different display modes according to a positional relation between the region of the tagged body fluid and a boundary line, set in the tagged region; and
  - output a time-series of display MR images including the generated plurality of display MR images being displayed on the display.

* * * * *